US006337183B1

(12) United States Patent
Arenas et al.

(10) Patent No.: US 6,337,183 B1
(45) Date of Patent: *Jan. 8, 2002

(54) SCREEN FOR COMPOUNDS WITH AFFINITY FOR NUCLEIC ACIDS

(75) Inventors: Jaime E. Arenas, Lexington; James W. Lillie, Wellesley; Andrew Pakula, Lexington, all of MA (US)

(73) Assignee: Scriptgen Pharmaceuticals, Inc.

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/709,342

(22) Filed: Sep. 6, 1996

Related U.S. Application Data

(60) Provisional application No. 60/003,406, filed on Sep. 8, 1995.

(51) Int. Cl.[7] .......................... C12Q 1/68; C07H 21/02

(52) U.S. Cl. ................... 435/6; 536/23.1; 536/24.31

(58) Field of Search ............... 435/6, 77.78; 536/23.1, 536/24.31

(56) References Cited

U.S. PATENT DOCUMENTS

| | | | | |
|---|---|---|---|---|
| 4,859,609 A | | 8/1989 | Dull et al. ................ 436/501 |
| 5,118,801 A | * | 6/1992 | Lizardi et al. ............... 435/6 |
| 5,200,504 A | | 4/1993 | Ghadiri ...................... 530/304 |
| 5,270,163 A | * | 12/1993 | Gold et al. .................... 435/6 |
| 5,306,619 A | * | 4/1994 | Edward et al. ............... 435/6 |
| 5,312,921 A | | 5/1994 | Glazer et al. ............... 546/108 |
| 5,325,295 A | | 6/1994 | Fratantoni et al. ..... 364/413.08 |
| 5,348,941 A | | 9/1994 | Middaugh et al. ............ 514/12 |
| 5,496,938 A | | 3/1996 | Gold et al. ................. 536/22.1 |
| 5,506,097 A | | 4/1996 | Potter et al. .................... 435/4 |
| 5,514,546 A | | 5/1996 | Kool ............................... 435/6 |
| 5,561,222 A | | 10/1996 | Keene et al. ............... 530/350 |
| 5,567,588 A | * | 10/1996 | Gold et al. .................... 435/6 |
| 5,580,722 A | | 12/1996 | Foulkes et al. ................ 435/6 |
| 5,585,277 A | | 12/1996 | Bowie et al. ............... 436/518 |
| 5,679,582 A | | 10/1997 | Bowie et al. ............... 436/518 |
| 5,712,096 A | * | 1/1998 | Stern et al. .................... 435/6 |
| 6,020,141 A | | 2/2000 | Pantoliano et al. .......... 435/7.1 |

FOREIGN PATENT DOCUMENTS

| | | |
|---|---|---|
| EP | 0 613 007 A2 | 8/1994 |
| WO | WO 92/03542 | 3/1992 |
| WO | WO 93/14781 | 8/1993 |
| WO | WO 97/42500 | 11/1997 |

OTHER PUBLICATIONS

Green et al., J. Mol. Biol. 235:237–247 (1994).*
Matthews et al., Anal. Biochem. 169:1–25 (1988).*
Totsuka et al., BBRC 205(1):168–173 (Mar. 8, 1995).*
Zapp et al., Cell 74:969–978, Sep. 1993.*
Andrew A. Pakula, Genetic Analysis of Protein Stability and Function, Annu. Rev. Genet. 1989, 23:289–310.
Walter H. Moos, Grant D. Green and Michael R. Pavia, Chapter 33, Recent Advances in the Generation of Molecular Diversity, Annual Reports in Medicinal Chemistry pp. 315–324 (1993).
Eric M. Gordon, et al., Journal of Medicinal Chemistry, Applications of Combinatorial Technologies to Drug Discovery. 2. Combinatorial Organic Synthesis, Library Screening Strategies, and Future Directions, vol. 37, No. 10, (1994).
Mark A. Gallop, et al., Journal of Medicinal Chemistry, Applications of Combinatorial Technologies to Drug Discovery. 1. Background and Peptide Libraries, vol. 37, No. 9 (1994).
James J. Devlin, Random Peptide Libraries: A Source Specific Protein Binding Molecules, Science, vol. 245 (1990).
P.C. Weber, et al., Structure–Based Design of Synthetic Azobenzene Ligands For Streptavidin, Journal of the Chemical Society, vol. 116 (1994).
Frederick G. Walz, Jr., et al., Spermine Stabilization of Folded Ribinuclease $T_1$, The Journal of Biological Chemistry 265, pp. 7127–7137 (1990).
Kit S. Lam, et al., A New Type of Synthetic Peptide Library For Identifying Ligand–Binding Activity, Nature, vol. 354 pp. 82–84 (1991).
C. Nick Pace, A Comparison of the Effectiveness of Protein Denaturants For B–Lactoglobulin and Ribonuclease, Archives of Biochemistry and Biophysics, vol. 199, No. 1, Jan. 1980, pp. 270–276.
P.K. Tsai, et al., Formulation Design of Acidic Fibroblast Growth Factor, Pharmaceutical Research, vol. 10, No. 5 (1993).
Baumann et al., *Eur. J. Biochem.*, 170:267–272, 1987.
Draper et al., *Meth. Enzymol.*, 259:281–305, 1995.
Gassen, *Prog. Nuc. Acid Res. and Molec. Bio.*, 24:57–83, 1980.
Sanford et al., *Nuc. Acids Res.*, 16:10643–10655, 1988.
Morton et al., *Biochemistry* 34:8513 (1995).
Erikson et al., *Nature* 335:371 (1992).
Derwent Publications. Abstract No. 75–43214W.
Eftink, *Biophys. J.*, 66:482–501 (1994).
Grant, S.K. et al., *Biochemistry* 31:9491–9501 (1992).
Randall, LL., *Science* 257:241–245 (1992).
Brandts et al. *Biochemistry* 29:6927 (1990).
Parsell, D.A. and Sauer, R.T., *J. Biol. Chem.* 264: 7590–7595 (1989).

(List continued on next page.)

Primary Examiner—Stephanie W. Zitomer
(74) Attorney, Agent, or Firm—Darby & Darby

(57) ABSTRACT

The present invention provides methods for high-throughput screening for bioactive compounds, in particular those that bind to RNA sequences involved in the pathogenesis of disease or in regulation of a physiological function. The methods involve measuring the conformation of an RNA target in the presence and absence of test ligands, and identifying as a ligand any test ligand that causes a measurable change in target RNA conformation.

19 Claims, 24 Drawing Sheets

OTHER PUBLICATIONS

Pace, C.N. and McGrath, T., *J. Biol. Chem.* 255:3862–3865 (1980).
Green, S.M. et al, *J. Biol. Chem.* 266:21474 (1991).
Wagenhofer, M. et al, *Anal Biochem.* 175: 422–432 (1988).
Casas–Finet, J.R. et al., *J. Mol. Biol.* 229: 873–889 (1993).
Kuwajima, K. et al., *Int. J. Peptide Protein Res.* 27: 18–27 (1986).
Lapadat, M.A. and Spremulli, L.L., *J. Biol. Chem.* 264:5510–5514 (1989).
Feng, Y. and Sligar, S.G., *Biochemistry.* 30: 10150–10155 (1991).
Tanigaki, N. et al., Human Immunology 36: 119–127 (1993).
Rosengart, et al, *Biochem. Biophys. Res. Commun.* 152: 442–440 (1988).
Chavan et al, *Biochemistry* 33:7193 (1994).
Airas, Kalervo R., *Biochim. Biophys. Acta* 452:193–200 (1976).
Wang, Zhen–Yuan *J. Biol. Chem.* 268:20785–20790 (1993).
Grimialdi, S. et al. *Biochemistry* 21:145–151 (1982).
Zahnley, J.C., *J. Inorganic Biochem.* 15: 67–78 (1981).
Doyle, R.J. et al., *Carbohydrate Res.* 46: 111–118 (1976).
Kahn, Theodore., W., Biochemistry 31:8829–8839 (1992).
Fernandez–Ballester, G. et al., *Biochem. J.* 228:421–426 (1992).
Lee, Heeyong, et al., *FEBS Letts.* 339:;165–167 (1994).
Harrington, J.P., *Int. J. Biochem.* 24:275–280 (1992).
Davidson, et al., Proc. Natl, Acad. Sci. USA 91:2146–2150 (1994).
Scott et al., *Science* 249:386 (1990).
Weber et al., *J. Am. Chem. Soc.* 16:2717 (1994).
Brandts et al., *American Laboratory* 22:30 (1990).
Bouvier et al, *Science* 265:398 (1994).
Schellman, *Biopolymers* 14:999 (1975).
Schellman, *Biophysical Chem.* 45:273 (1993).
Richard L. Horwitz, Memorandum Opinion in Scriptgen Pharmaceutical Inc. v. 3–Dimensional Pharmaceuticals; Civil Action No. 98–583–GMS, United States District Court for the District of Delaware; Dec. 15, 1999.
John P. Harrington. Int. J. Biochem vol. 24, No. 2, pp. 275–280 (1992).
Bertrand Friguet et al. "Immunochemical analysis of protein conformation" in *Protein Structure a Practical Approach*, ed. T.E. Creighton.(IRL Press at Oxford University Press, New York). pp. 323–348.
Eugene A. Permyakov et al., Biophysical Chemistry 32:37–42 (1988).
David B. Volkin et al., The Effect of Polyanions on the Stabilization of Acidic Fibroblast Growth Factor, Proceedings of the Ninthe International Biochemistry Symposium and Exposition, American Chemical Society, 1992, cover pages and pages 299–302.
C. Nick Pace et al., Ribonuclease T1 Is Stabilized by Cation and Anion Binding, Biochemistry 1988, 27, 3242–3246.
Ferscht, *Curr., Opinion in Struc. Biol.* 7:3 (1997).
Burke et al., Biochemistry, 32:6419–6426, 1993.
Volkin et al., Archives of Biochemistry and Biophysics, 300:30–41, 1993.
Hu et al., Biochemistry, 31:4876–82, 1992.
Copeland et al., Archives of Biochemistry and Biophysics, 289:53–61, 1991.
Dabora, et al., J. Biol. Chem., 266:23637–40, 1991.
Pace, TIBS 15, Jan. 1990, 14–17.
Keating et al., Biochemistry, 27:5240–5, 1988.
Allen and Wong, Arch. Biochem. Biophys., 249:137–147, 1986.
Busby and Ingham, Biochim. Biophys. Acta, 871:61–71, 1986.
Pace and Creighton, J. Mol. Biol., 188:477–486, 1986.
Schnarr and Maurizot, Biochim. Biophys. Acta, 702:155–162, 1982.
Klesov and Gerasimas, Biokhimiia, 44:1084–92, 1979.
Oobatake et al., J. Biochem., 86:65–70, 1979.
Blazyk and Lam, Biochemistry, 15:2843–8, 1976.
DeFlora et al., Ital. J. Biochem., 24:147–61, 1975.
Takahasi, J. Biochem., 75:201–204, 1974.
Expert Report of James R. Broach on Issues of Patent Invalidity, Scriptgen Pharmaceutical v. 3–Dimensional Pharmaceutical, U.S. District Court, Delaware, Nov. 1, 1999.
Opening Brief in Support of Defendant's Motion for Summary Judgment of Invalidity, Scriptgen Pharmaceuticals v. 3–Dimensional Pharmaceuticals, U.S. District Court, Delaware, Jan. 7, 2000.
Sciptgen Pharmaceuticals, Inc.'s Answering Brief in Opposition to Defendant's Motion for Summary Judgment of Invalidity, Scriptgen Pharmaceuticals v. 3–Dimensional Pharmaceuticals, U.S. District Court, Delaware, Feb. 1, 2000.
Defendant's Reply Brief in Support of Defendant's Motion for Summary Judgment of Invalidity, Scriptgen Pharmaceuticals v. 3–Dimensional Pharmaceuticals, U.S. District Court, Delaware, Feb. 28, 2000.
Bowie, Identifying Determinants of Folding and Activity for a Protein of Unknown Structure, B.A., Chemistry, Carleton College (1981), Submitted to the Department of Biology in Partial Fulfillment of the Requirements for the Degree of Doctor of Philosphy at the Massachusetts Institute of Technology, May 1989.
Enna, "Radioligand Binding Assays", Principals and Methods in Receptor Binding, pp. 13–33, Plenum Publishing Corp. (1984).
Fuller and Steranka, "Drug Discovery at the Enzyme Level", Drug Discovery and Development, pp. 177, 198, Humana Press (1987).
Enna, "Biochemical Approaches for Evaluating Drug–Receptor Interactions", Drug Discovery and Development, pp. 151–176, Humana Press (1987).
Baldwin, "Drug Design", Drug Discovery and Development, pp. 33–71, Humana Press (1987).
Williams and Malick, "Drug Discovery and Development", pp. 3–29, Drug Discovery and Development, Humana Press (1987).
Kinnier, "Receptor Binding as a Method for Drug Discovery", Drug Discovery and Development, Humana Press (1987).
Bieth et al. Biochemical Medicine, 11:350–357, 1974.
Gething and Sambrook, Nature, 355:33–45, 1992.
Hardy and Randall, Science, 251:439–443, 1991.
Crothers, D.M., Draft Opinion, Scriptgen Pharmaceuticals v. 3–Dimensional Pharmaceuticals, U.S. District Court, Delaware, pp. 1–15, Oct. 20, 1999.
Chen, L. et al., Anal Chem., 64:3018–3023, 1992.
Silverman, L. et al., Current Opinion in Chemical Biology-chemistry, 397–403, 1998.
Broach, J.R. and Thorner, J., Nature, 384 (Supp. 7):14–16, 1996.

Pakula A.A., "A Genetic and Biological Analysis of the Bacteriophage λ Cro Protein", B.S., Biol. And Chem., Tufts Univ. (1980), Submitted to the Department of Biology in Partial Fulfillment of the Requirements for the Degree of Doctor of Philosphy at the Massachusetts Institute of Technology, Sep. 1988.
Alderman, E.M., Director, Pharmaceutical Research, , New Ventures, Zymark Corporation, "Abbreviating the Assay Development Process through Scaleable Automation Technology"
Wainer, I.W., Professor of Pharmacology, Georgetown University Medical Center, "Immobilized Receptor–Based Liquid Chromatographic Stationary Phases for Rapid On–Line Screening"
Zhang, Y. et al., Analytical Biochemistry, 264:22–25, 1998.
Volkin D.B. et al., Biochemistry, 33:7193–7202, 1994.
Markovits et al., Analytical Biochemistry, 94:259–164 (1979).
Rye et al., Nucleic Acids Research, 20:2803–2812 (1992).
Calcutt et al., Gene, 137(1):77–83 (1993) (see entire article).
Pesce et al., Nucleic Acids Research, 22(4):656–661, Feb. 25, 1994 (see entire article).

* cited by examiner

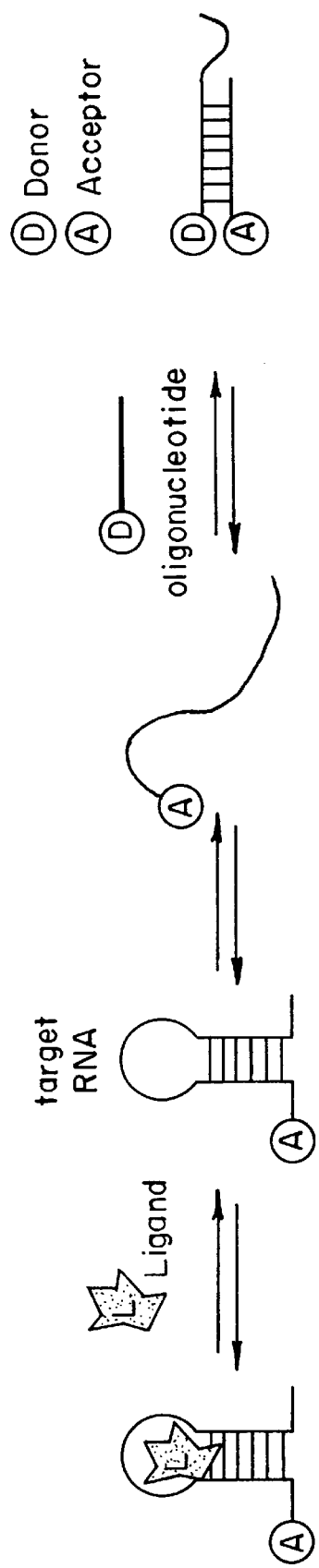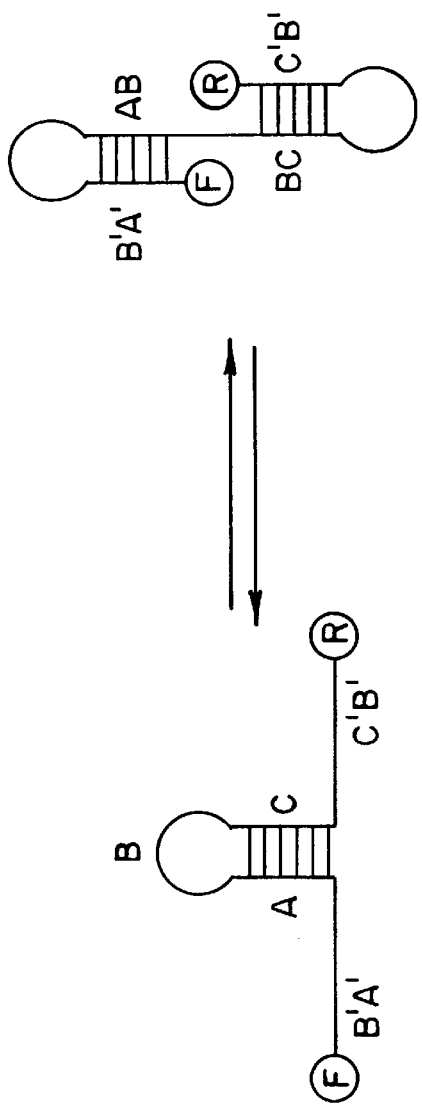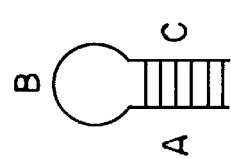
FIG. 5
FIG. 23
FIG. 22

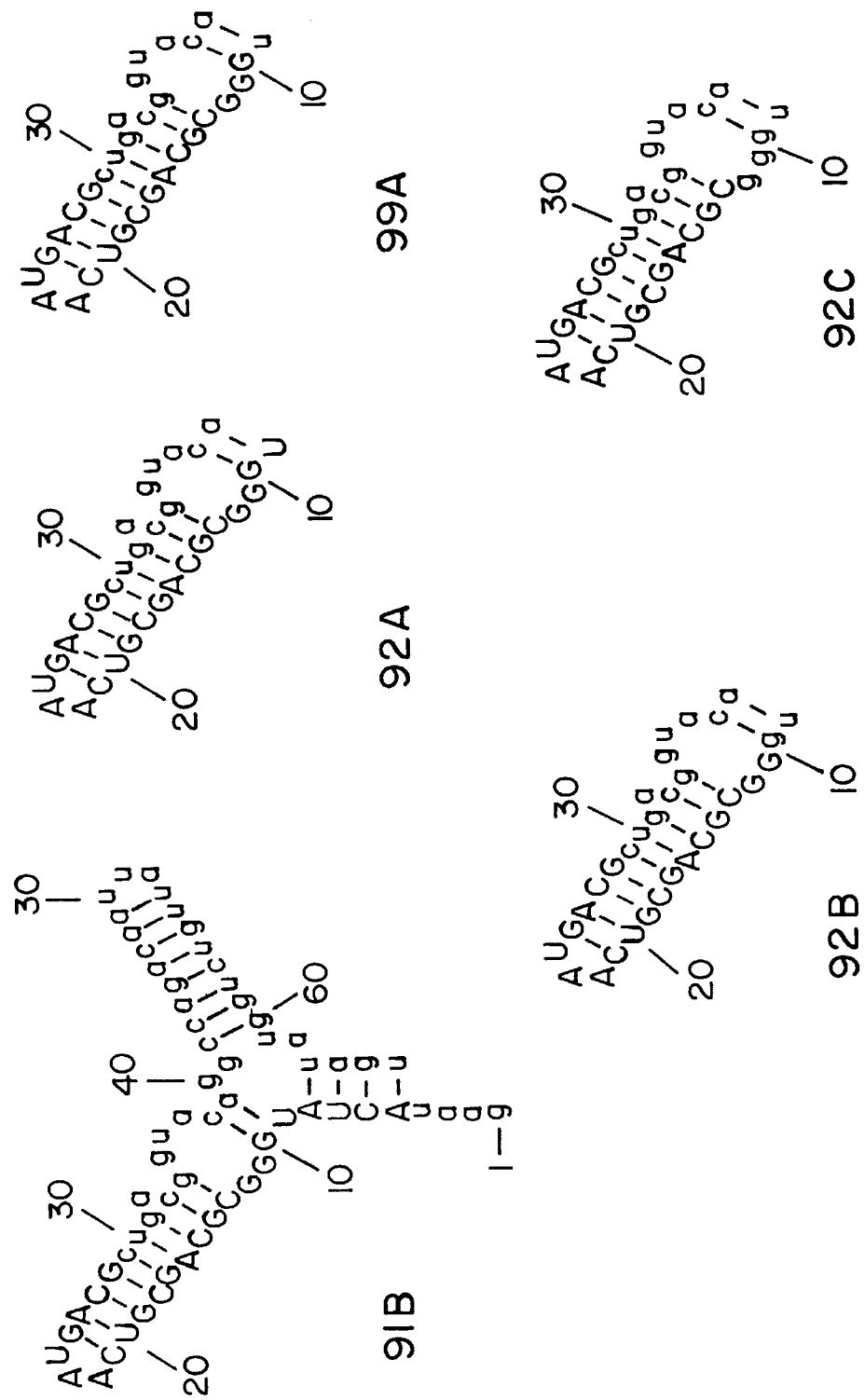

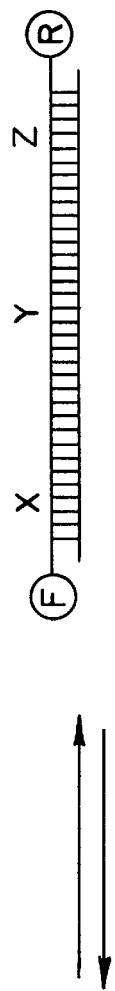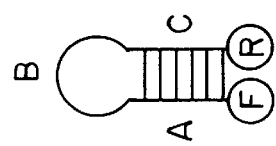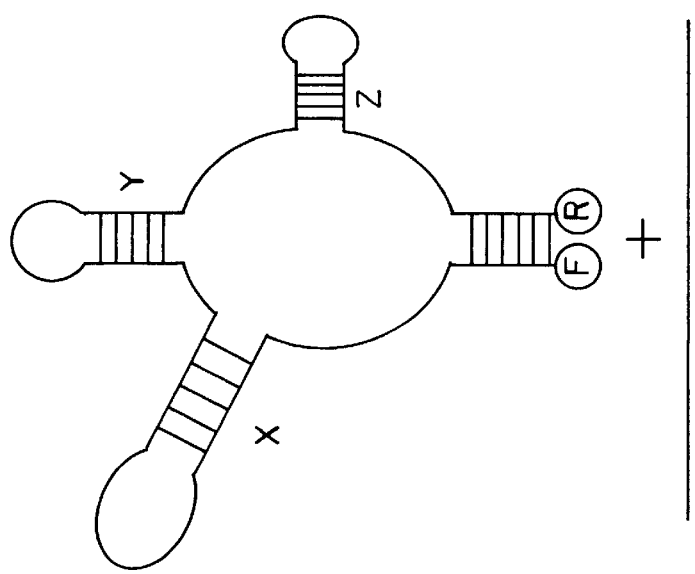
FIG. 24
FIG. 25

SCREEN FOR COMPOUNDS WITH AFFINITY FOR NUCLEIC ACIDS

This application claims priority from provisional application serial no. 60/003,406, filed Sep. 8, 1995.

FIELD OF INVENTION

This invention pertains to novel methods for high-throughput screening for pharmaceutical compounds, in particular those that bind to RNA sequences involved in the pathogenesis of disease or in regulation of a physiological function.

BACKGROUND OF THE INVENTION

Pharmaceuticals can be developed from lead compounds that are identified through a random screening process directed towards a target, such as a nucleic acid or a protein receptor. Large scale screening approaches can be complicated by a number of factors. First, many assays are laborious or expensive to perform. Assays may involve experimental animals, cell lines, or tissue cultures that are difficult or expensive to acquire or maintain. These considerations often place practical limitations on the number of compounds that reasonably can be screened. Thus, those employing random screening methods are frequently forced to limit their search to those compounds for which some prior knowledge suggests that the compounds are likely to be effective. This strategy limits the range of compounds tested, and many useful drugs may be overlooked.

Furthermore, the specificity of many biochemical assays may exclude a wide variety of useful chemical compounds, because the interactions between the ligand and the target are outside the scope of the assay. With such a specific assay, many potential pharmaceuticals may not be detected.

Finally, in most existing biochemical screening approaches to drug discovery, the system in question must be well-characterized before screening can begin. Consequently, biochemical screening for therapeutic drugs directed against many targets must await detailed biochemical characterization, a process that generally requires extensive research.

The present invention pertains specifically to the use of RNA targets in high-throughput screening methods for identification of useful ligands. The invention takes advantage of the existence of higher-order structures in naturally-occurring and synthetic RNA molecules. For example, RNA exists in both single stranded and helical duplex forms. These duplexes may be distorted by loops, bulges, base triples and junctions between helices. The structural diversity of RNA is far greater than that of DNA, and similar to that of proteins, making RNA a likely target for binding of small molecules (reviewed in Wyatt and Tinoco. *The RNA World*, Gesteland and Atkins, eds., Cold Spring Harbor, 1993, pp. 465–496-A.

Small molecules can bind RNA with high affinity and specificity and can block essential functions of the bound RNA. The best example of such molecules are antibiotics such as erythromycin and aminoglycosides. The first suggestion that some antibiotic translation inhibitors interact specifically with RNA was the genetic mapping of resistance to kanamycin and gentamicin to the methylation of 16S RNA (Thompson et al., *Mol. Gen. Genet.* 201:168, 1985). Erythromycin binds to bacterial RNA and releases peptidyl-tRNA and mRNA (Menninger et al., *Mol. Gen. Genet.* 243:225, 1994). 2-DOS-containing aminoglycosides bind specifically to the structures of HIV RNA known as the RRE, block binding of the HIV Rev protein to this RNA, and thereby inhibit HIV replication in tissue culture cells (Zapp et al., *Cell* 74:969, 1993). In addition, although aminoglycosides have long been developed as translation inhibitors, they were only recently shown to bind to rRNA in the absence of proteins (Purohit and Stern, *Nature* 370:659, 1994). Hygromycin B inhibits coronaviral RNA synthesis and is thought to do so by binding to the viral RNA and blocking specifically the translation of viral RNA (Macintyre et al., *Antimicrob. Agents Chemother.* 35:2630, 1991).

Existing assays for ligands of nucleic acids, such as, for example, methods that use equilibrium dialysis, differential scanning calorimetry, viscometric analyses, or UV melting, have not been used in high-throughput applications. Thus, prior to the present invention, random screening approaches for non-oligonucleotide ligands of RNA were limited to compounds for which some prior knowledge suggested that they might be effective. This strategy has been successful (Zapp et al., 1993), but is limited in the range of compounds that can be tested on a practical scale.

U.S. Pat. No. 5,270,163 describes the SELEX system for the identification of oligonucleotides that bind specific targets. In this system, random oligonucleotides are affinity-selected and amplified, followed by several cycles of re-selection and amplification. This method, however, is limited to screening for oligonucleotide ligands and cannot be applied in reverse, i.e., to search for non-oligonucleotide ligands that bind to nucleic acids.

U.S. Pat. No. 5,306,619 discloses a screening method to identify compounds that bind particular DNA target sequences. In this method, a test nucleic acid is constructed in which the target sequence is placed adjacent to a known protein-binding DNA sequence. The effect of test compounds on the binding of the cognate protein to the protein-binding DNA sequence is then measured. This method requires conditions in which melting of DNA hybrids and unfolding of DNA structure do not occur. RNA, by contrast, can undergo much more dramatic variations in patterns of base-pairing and overall conformation.

Thus, there is a need in the art for efficient and cost-effective high-throughput methods for random screening of large numbers of non-oligonucleotide small molecules for their ability to bind physiologically, medically, or commercially significant RNA molecules.

SUMMARY OF THE INVENTION

The present invention encompasses high-throughput screening methods to identify ligands that bind any predetermined target RNA. The methods are carried out by the steps of: selecting as test ligands a plurality of compounds not known to bind to the target RNA sequence; incubating the target RNA sequence in the presence of each of the test ligands to produce a test combination; incubating the target RNA sequence in the absence of a test ligand to produce a control combination; measuring the conformation of the target RNA in each combination; selecting as a ligand any test ligand that causes a measurable change in the target RNA conformation in the test combination relative to the control combination; and repeating the method with a plurality of said test ligands to identify a ligand that binds to the target RNA sequence. Ligands identified by the methods of the present invention may cause the target RNA to change from a less folded to more folded conformation, from a more folded to less folded conformation, or from a first folded conformation to a second, alternative, folded conformation.

Furthermore, the test and control combinations may be subjected to conditions that, in the absence of ligands (i.e., in the control combination), denature a detectable fraction of the target RNA.

In practicing the present invention, the effect of test ligands on the folding state of the target RNA is determined using well-known methods, including without limitation hybridization with complementary oligonucleotides, treatment with conformation-specific nucleases, binding to matrices specific for single-stranded or double-stranded nucleic acids, and fluorescence energy transfer between fluorescence probes. In one embodiment, the target RNA is radiolabelled and incubated with a biotinylated oligonucleotide that preferentially hybridizes to a particular conformation of the target RNA; following capture of biotinylated molecules using immobilized streptavidin, the extent of hybridization can be readily quantified by measurement of immobilized radiolabel. In another embodiment, the target RNA contains two different fluorescence probes in which the fluorescence emission wavelength maximum of the first probe overlaps the fluorescence absorption maximum of the second probe. The probes are positioned within the target RNA so that the efficiency of fluorescence energy transfer between the probes is dependent upon the target RNA conformation.

A "measurable change" in target RNA conformation as detected by any of the above or other methods is one in which the difference in the measured parameter between the test and control combinations is greater than that expected due to random statistical variation.

BRIEF DESCRIPTION OF THE DRAWINGS

FIG. 5 is a graphic illustration of the use of intermolecular fluorescence energy transfer to monitor hybridization.

FIG. 14C is a graphic illustration of the structure of HIV RRE RNA target (full length shown at left) showing in bold-face uppercase the sequences that are complementary to oligonucleotides 91B, 92A, 99A, 92B, and 92C.

FIG. 22 is a graphic illustration of a simple stem-loop RNA structure.

FIG. 23 is a graphic illustration of a complex RNA structure containing fluorescein and rhodamine labels, which can fold into mutually exclusive folding patterns.

FIG. 24 is a graphic illustration of a simple stem-loop RNA structure containing fluorescein and rhodamine labels.

FIG. 25 is a graphic illustration of the hybridization reaction between a complex RNA structure labelled with both fluorescein and rhodamine and a complementary DNA oligonucleotide.

DETAILED DESCRIPTION OF THE INVENTION

Figure 1:
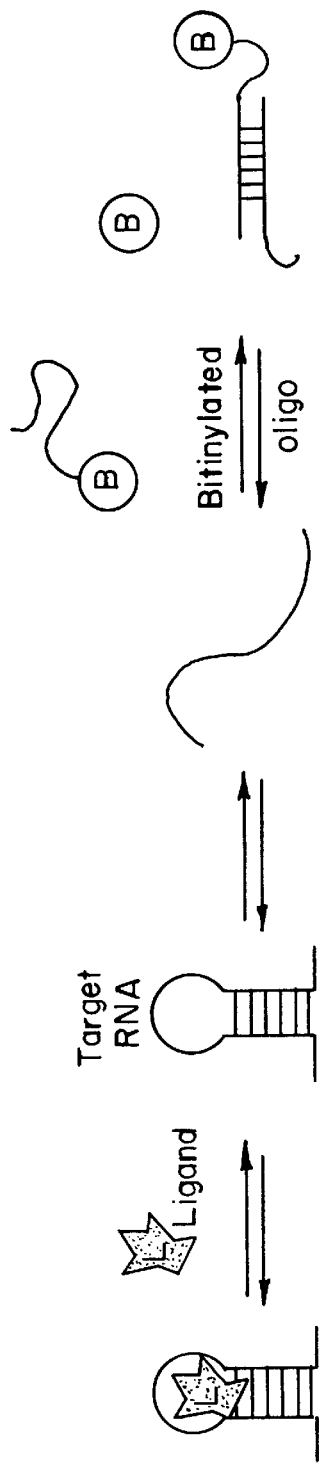
FIG. 1 is a graphic illustration of the reaction between a biotinylated complementary oligonucleotide and a labelled target RNA.

All patent applications, patents, and literature references cited in this specification are hereby incorporated by reference in their entirety. In case of conflict, the present description, including definitions, will prevail.

Definitions

As used herein, the term "ligand" refers to an agent that binds a target RNA. The agent may bind the target RNA when the target RNA is in a native or alternative conformation, or when it is partially or totally unfolded or denatured. According to the present invention, a ligand can be an agent that binds anywhere on the target RNA. Therefore, the ligands of the present invention encompass agents that in and of themselves may have no apparent biological function, beyond their ability to bind to the target RNA.

As used herein, the term "test ligand" refers to an agent, comprising a compound, molecule or complex, which is being tested for its ability to bind to a target RNA. Test ligands can be virtually any agent, including without limitation metals, peptides, proteins, lipids, polysaccharides, small organic molecules, nucleotides (including non-naturally occurring ones) and combinations thereof. Small organic molecules have a molecular weight of more than 50 yet less than about 2,500 daltons, and most preferably less than about 400 daltons. Preferably, test ligands are not oligonucleotides. Complex mixtures of substances such as natural product extracts, which may include more than one test ligand, can also be tested, and the component that binds the target RNA can be purified from the mixture in a subsequent step.

Test ligands may be derived from large libraries of synthetic or natural compounds. For example, synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or MycoSearch (N.C.), or are readily producible. Additionally, natural and synthetically produced libraries and compounds are readily modified through conventional chemical, physical, and biochemical means. For example, the compounds may be modified to enhance efficacy, stability, pharmaceutical compatibility, and the like.

For example, once a peptide ligand has been identified using the present invention, it may be modified in a variety of ways to enhance its stability, such as using an unnatural amino acid, such as a D-amino acid, particularly D-alanine, or by functionalizing the amino or carboxyl terminus, e.g., for the amino group, acylation or alkylation, and for the carboxyl group, esterification or amidification, or through constraint of the peptide chain in a cyclic form, or through other strategies well known to those skilled in the art.

As used herein, the term "target RNA" refers to a RNA sequence for which identification of a ligand or binding partner is desired. Target RNAs include without limitation sequences known or believed to be involved in the etiology of a given disease, condition or pathophysiological state, or in the regulation of physiological function. Target RNAs may be derived from any living organism, such as a vertebrate, particularly a mammal and even more particularly a human, or from a virus, bacterium, fungus, protozoan, parasite or bacteriophage. Target RNA may comprise wild type sequences, or, alternatively, mutant or variant sequences, including those with altered stability, activity, or other variant properties, or hybrid sequences to which heterologous sequences have been added. Furthermore, target RNA as used herein includes RNA that has been chemically modified, such as, for example, by conjugation of biotin, peptides, fluorescent molecules, and the like.

Target RNA sequences for use in the present invention are typically between about 5 and about 500 nt, preferably between about 30 and about 100 nt, and most preferably about 50 nt. Target RNAs may be isolated from native sources, or, more preferably, are synthesized in vitro using conventional polymerase-directed cell-free systems such as those employing T7 RNA polymerase.

As used herein, "test combination" refers to the combination of a test ligand and a target RNA. "Control combination" refers to the target RNA in the absence of a test ligand.

As used herein, the "folded state" of a target RNA refers to a native or alternative conformation of the sequence in the absence of denaturing conditions. The folded state of an RNA encompasses both particular patterns of intramolecular base-pairing, as well as particular higher-order structures. Without wishing to be bound by theory, it is believed that certain target RNAs may achieve one of several alternative folded states depending upon experimental conditions (including buffer, temperature, presence of ligands, and the like).

As used herein, the "unfolded state" of a target RNA refers to a situation in which the RNA has been rendered partially or completely single-stranded relative to its folded state(s) or otherwise lacks elements of its structure that are present in its folded state. The term "unfolded state" as used herein encompasses partial or total denaturation and loss of structure.

As used herein, a "measurable change" in RNA conformation refers to a quantity that is empirically determined and that will vary depending upon the method used to monitor RNA conformation. The present invention encompasses any difference between the test and control combinations in any measurable physical parameter, where the difference is greater than expected due to random statistical variation.

As used herein, the acronym SCAN refers to "Screen for Compounds with Affinity for Nucleic Acids", a generic description of the present invention.

The present invention encompasses high-throughput screening methods for identifying a ligand that binds a target RNA. If the target RNA to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target RNA from a mixture. The present invention also relates to ligands identified by the present method and their therapeutic uses (for diagnostic, preventive or treatment purposes) and uses in purification and separation methods.

According to the present invention, a ligand for a target RNA is identified by its ability to influence the extent or pattern of intramolecular folding or the rate of folding or unfolding of the target RNA. Experimental conditions are chosen so that the target RNA is subjected to unfolding or rearrangement. If the test ligand binds so the target RNA under these conditions, the relative amount of folded:unfolded target RNA, the relative amounts of one or another of multiple alternative folded states of the target RNA, or the rate of folding or unfolding of the target RNA in the presence of the test ligand will be different, i.e., higher or lower, than that observed in the absence of the test ligand. Thus, the present method encompasses incubating the target RNA in the presence and absence of a test ligand. This is followed by analysis of the absolute or relative amounts of folded vs. unfolded target RNA, the relative amounts of specific folded conformations, or of the rate of folding or unfolding of the target RNA.

An important feature of the present invention is that it may detect any compound that binds to any region of the target RNA, not only to discrete regions that are intimately involved in a biological activity or function.

In practicing the present invention, the test ligand is combined with a target RNA, and the mixture is maintained under appropriate conditions and for a sufficient time to allow binding of the test ligand to the target RNA. Experimental conditions are determined empirically for each target RNA. When testing multiple test ligands, incubation conditions are chosen so that most ligand:target RNA interactions would be expected to proceed to completion. In general, the test ligand is present in molar excess relative to the target RNA. As discussed in more detail below, the target RNA can be in a soluble form, or, alternatively, can be bound to a solid phase matrix.

The time necessary for binding of target RNA to ligand will vary depending on the test ligand, target RNA and other conditions used. In some cases, binding will occur instantaneously (e.g., essentially simultaneous with combination of test ligand and target RNA), while in others, the test ligand-target RNA combination is maintained for a longer time e.g. up to 12–16 hours, before binding is detected. When many test ligands are employed, an incubation time is chosen that is sufficient for most RNA:ligand interactions, typically about one hour. The appropriate time will be readily determined by one skilled in the art.

Other experimental conditions that are optimized for each RNA target include pH, reaction temperature, salt concentration and composition, divalent cation concentration and composition, amount of RNA, reducing agent concentration and composition, and the inclusion of non-specific protein and/or nucleic acid in the assay. An important consideration when screening chemical or natural product libraries is the response of the assay to organic solvents (e.g., dimethyl sulfoxide, methanol or ethanol) commonly used to resuspend such materials. Accordingly, each RNA is tested in the presence of varying concentrations of each of these organic solvents. Finally, the assay may be particularly sensitive to certain types of compounds, in particular intercalating agents, that commonly appear in chemical and especially natural product libraries. These compounds can often have potent, but non-specific, inhibitory activity. Some of the buffer components and their concentrations will be specifically chosen in anticipation of this problem. For example, bovine serum albumin will react with radicals and minimize surface adsorption. The addition of non-specific DNA or RNA may also be necessary to minimize the effect of nucleic acid-reactive molecules (such as, for example, intercalating agents) that would otherwise score as "hits" in the assay.

Binding of a test ligand to the target RNA is assessed by comparing the absolute amount of folded or unfolded target RNA in the absence and presence of test ligand, or, alternatively, by determining the ratio of folded:unfolded target RNA or change in the folded state of the target RNA, or the rate of target RNA folding or unfolding in the absence and presence of test ligand. If a test ligand binds the target RNA (i.e., if the test ligand is a ligand for the target RNA), there may be significantly more folded, and less unfolded, target RNA (and, thus, a higher ratio of folded to unfolded target RNA) than is present in the absence of a test ligand. Alternatively, binding of the test ligand may result in significantly less folded, and more unfolded, target RNA than is present in the absence of a test ligand. Another possibility is that binding of the test ligand changes the pattern or properties of alternative RNA folded structures. Similarly, binding of the test ligand may cause the rate of target RNA folding or unfolding to change significantly or may change the rate of acquisition of an alternative structure.

In either case, determination of the absolute amounts of folded and unfolded target RNA, the folded:unfolded ratio, or the rates of folding or unfolding, may be carried out using any method, including without limitation hybridization with complementary oligonucleotides, treatment with conformation-specific nucleases, binding to matrices specific for single-stranded or double-stranded nucleic acids, and fluorescence energy transfer between adjacent fluorescence probes. Other physico-chemical techniques may also be used, either alone or in conjunction with the above methods; these include without limitation measurements of circular dichroism, ultraviolet and fluorescence spectroscopy, and calorimetry. However, it will be recognized by those skilled in the art that each target RNA may have unique properties that make a particular detection method most suitable in a particular application.

For the purposes of high-throughput screening, the experimental conditions are adjusted to achieve a threshold proportion of test ligands identified as "positive" compounds or ligands from among the total compounds screened. This threshold is set according to two criteria. First, the number of positive compounds should be manageable in practical terms. Second, the number of positive compounds should reflect ligands with an appreciable affinity towards the target RNA. A preferred threshold is achieved when 0. 1% to 1% of the total test ligands are shown to be ligands of a given target RNA.

Methods for Detection of RNA Folding

The present invention may be practiced using any of a large number of detection methods well-known in the art. For example, an oligonucleotide (whether DNA or RNA) can be designed so that it will hybridize to a particular RNA target only when the RNA is in an unfolded conformation or to single-stranded regions in an otherwise folded conformation. In some embodiments, hybridization of an oligonucleotide to a target RNA is allowed to proceed in the absence and presence of test ligands (i.e., in control and test combinations, respectively), after which the extent of hybridization is measured using any of the methods well-known in the art. Typically, an increase or decrease in hybridization that is greater than that expected due to random statistical variation in the test vs. control combination indicates that the test ligand binds the target RNA. Other useful methods to measure the extent of folding of the target RNA include without limitation intramolecular fluorescence energy transfer, digestion with conformation-specific nucleases, binding to materials specific for either single-stranded or double-stranded nucleic acids (such as, nitrocellulose or hydroxylapatite), measurement of biophysical properties indicative of RNA folded structure (such as UV, Raman, or CD spectrum, intrinsic fluorescence, sedimentation rate, or viscosity), measurement of the stability of a folded RNA structure to heat and/or formamide denaturation (using methods such as, spectroscopy or nuclease susceptibility), and measurement of protein binding to adjacent reporter RNA. Examples of these methods are disclosed in the following articles: Kan et al., *Eur.J.Biochem.* 168:635, 1987 (NMR); Edy et al., *Eur.J.Biochem.* 61:563, 1976, Yeh et al., *J.Biol.Chem.* 263:18213, 1988, Clever et al., *J. Virol.* 69: 2101, 1995, and Vigne et al., *J.Mol.Evol.* 10:77, 1977 (RNAases); Millar, *Biochim.Biophy.Acta* 174:32, 1969 (thermal melting, fluorescence polarization); and *Zimmerman Biochem.Z.* 344:386, 1966 and Dupont et al., *C.R.Acad.Sci.Hebd.Seances Acad.Sci.D.* 266:2234, 1968 (viscosity).

1. Gel Shift

A gel shift protocol, though nominally a low-throughput method, is an important tool for the initial selection of the assay configuration for oligonucleotide-based methods to be used with each particular target RNA. Typically, the target RNA is transcribed in vitro, using as template a DNA that contains the sequence for the T7-RNA polymerase promoter followed by a region encoding the target RNA, and [$^{32}$P]-UTP to produce radiolabelled RNA. Conditions for the T7 RNA polymerase transcription reaction using oligonucleotide templates have been described by Milligan et al., *Nuc. Acids Res.*, 15: 8783, 1987. The [$^{32}$P]-labelled target RNA is optionally heat denatured at 90° C. for 2 min and chilled on ice for 2 min, after which aliquots are incubated in the absence and presence of test ligands and increasing concentrations of a complementary oligonucleotide. The reaction mixtures are then resolved in polyacrylamide native gels containing or lacking the test ligands.

If a test ligand binds the target RNA, it will inhibit the formation of hybrids between the target and the complementary oligonucleotide. An example of this method is described in Example 1 below.

2. High Throughput Assays Using Streptavidin-biotin

In these embodiments, a biotin moiety is introduced into the complementary oligonucleotide or into the target RNA. This allows the use of capture methods that are based on the strong interaction between biotin and avidin, streptavidin (SA) or other derivatives of biotin-binding proteins (Wilchek et al., *Meth.Enzymol.*, 184:5–45, 1990). FIG. 1 illustrates the use of a biotinylated oligonucleotide and a labeled RNA target. Only those labelled RNA target molecules that are hybridized to the biotinylated oligonucleotide can become associated with the biotin binding protein.

The biotin moiety can be located at any position in the oligonucleotide, or there can be multiple biotin moieties per oligonucleotide molecule. The SA (or its derivatives or analogues) can be covalently attached to a solid support, or it can be added free in solution. The target RNA can be radiolabelled, for example, or labelled with a fluorophore such as fluorescein or rhodamine or any other label that can be readily measured.

Figure 2:
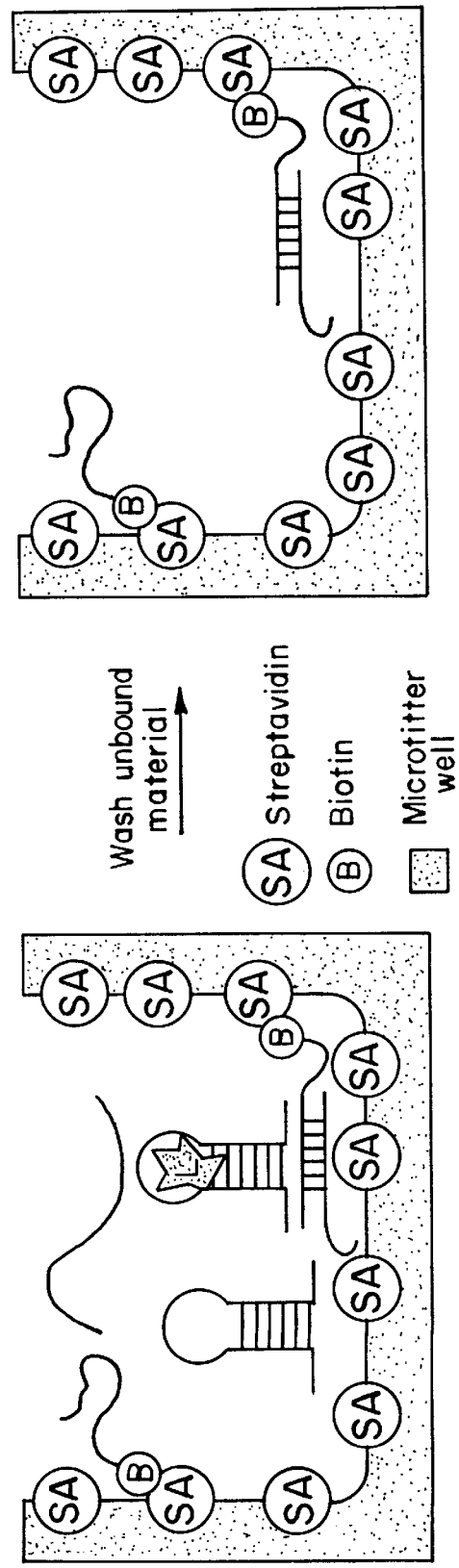
FIG. 2 is a graphic illustration of the use of streptavidin-coated plates in conjunction with a biotinylated oligonucleotide complementary to the target RNA.

SA coated plates: FIG. 2 illustrates the use of 96-well plates coated with SA, which are commercially available (Pierce, Rockford, Ill.). The reactions are first set up in a regular uncoated 96-well plate by mixing the labeled RNA target with the biotinylated oligonucleotide and the ligands to be tested. After an incubation period, the reaction mixture is transferred into a SA coated plate to allow binding of the biotin moiety to SA. Target RNA:oligonucleotide hybrids and free biotinylated oligonucleotide will bind to the wall of the plate through the SA-biotin interaction. Unbound material, including target RNA that is not associated with the oligonucleotide, is washed away with an excess of buffer. The target RNA remaining in the plate after the wash is quantified by an appropriate method, depending upon the nature of the label in the target RNA.

SA coated beads: In this embodiment, the SA is covalently attached to small beads of an inert material, such as, for example, sepharose (Pharmacia, Uppsala, Sweden), agarose (Sigma Chemical Co., St. Louis, Mo.), or Affigel (BioRad, Hercules, Calif.). A fixed amount of beads is added to each well containing the reaction mixture to allow binding of the hybrids. The beads are then washed to remove unbound material before quantitation.

SA coated paramagnetic beads: The washing step required when using SA-beads can be facilitated by using paramagnetic-SA coated beads (PMP-SA). These beads are commercially available (Promega, Madison, Wis.) and can be concentrated and held by a magnet. Positioning the magnet under the plate during washing steps concentrates and retains the beads at the bottom of the well during the washing procedure thus preventing loss of beads and allowing faster operation. An example of the use of this method is described in Example 2 below.

SA coated SPA beads and scintillant containing plates: Scintillation proximity assay (SPA) is a technology available from Amersham Corp. (Arlington Heights, Ill.) that can be used for measurement of hybridization. SA coated SPA beads contain a solid phase scintillant that can be excited by low energy isotopes in close proximity. In this embodiment, the target RNA is labelled with =$^3$H (whose weak radiation energy is virtually undetectable at distances of more than one micron unless the signal is amplified by a scintillant). When using SPA beads, only those radiolabelled molecules that bind to the SA-SPA-beads will be close enough to cause the scintillant to emit a detectable signal, while those molecules in solution will not contribute to the signal. Therefore, by using a biotinylated oligonucleotide and a $^3$H labelled RNA target, it is possible to determine the amount of hybrids formed in the reaction by adding SA-SPA beads to the reaction and then counting in a LSC-counter after a brief binding incubation period. Plates coated with SA (which contain a scintillant attached to the surface of the wells) are also commercially available (Scintiplates®, Packard, Meriden, Conn.) can be used for this assay in place of SA-SPA beads.

Adsorption to nitrocellulose filters: This embodiment takes advantage of the fact that most proteins tightly adsorb to nitrocellulose filters. When using a biotinylated oligonucleotide and a labelled target RNA, free SA or a SA derivative such as SA:alkaline phosphatase conjugate (SA:AP), SA:β-galactosidase (SA:BG), or other SA-conjugate or fusion protein, is added to the reaction to allow binding to the biotin moiety in the oligonucleotide. Subsequently, the reaction is filtered through 96-well nitrocellulose filter plates (Millipore, Bedford, Mass., HATF or NC). Labeled target RNA hybridized to the biotinylated oligonucleotide is retained in the filter through the adsorption of SA or its derivative to the filter, while unhybridized RNA passes through. SA has been found to bind poorly to nitrocellulose filters; however, the present inventors have discovered that the use of SA conjugates or fusion proteins increases the adsorption of the protein to nitrocellulose. Therefore, the use of SA fusion proteins or conjugates is preferred. An example of the use of this method is described in Example 3 below.

3. High-throughput Assays Using Covalently Attached Proteins

Polypeptides and proteins can be covalently attached to the 5'-end of nucleic acids that have been treated with a carbodiimide to form an activated 5'-phosphorimidazolide derivative that will readily react with amines including those in polypeptides and proteins (Chu et al., *Nuc. Acids Res.*, 11:6513, 1983). Using this approach, any peptide or protein of choice can be covalently attached to the 5'-end of the RNA target or the complementary oligonucleotide used in the present invention. Non-limiting examples of embodiments that use this technique are described below.

Adsorption to nitrocellulose filters: With a peptide or protein covalently attached to the oligonucleotide and a labeled RNA target, or, conversely, with a peptide or protein covalently attached to the RNA target and a labeled oligonucleotide, hybridization can be quantified in essentially the same way as described above for the SA based capture of biotin containing hybrids in nitrocellulose filters. In this case, however, binding to the filter is via the peptide or protein adduct in the RNA target, or in the oligonucleotide.

Affinity binding to solid supports: All the techniques described above for the use of SA-biotin can be duplicated by using any of a number of other affinity pairs in place of SA and biotin. The adduct "Y" attached to the oligonucleotide (or target RNA) is capable of high affinity binding with a specific molecule "X" which is attached to a solid support. Activated resins (beads) and 96-well plastic plates for attachment of macromolecules or their derivatives are commercially available (Dynatech, Chantilly, Va.). X and Y can be a number of combinations including antigen-antibody, protein-protein, protein-substrate, and protein-nucleic acid pairs. Some of these pairs are shown in the following table:

| X | Y |
|---|---|
| Antigen/epitope | Specific antibody |
| Protein A | Immunoglobulin |
| Glutathione | Glutathione-S-transferase |
| Maltose | Maltose binding protein |
| RNA or DNA motif | Specific motif binding protein |

In most cases either component of the pair can be attached to the RNA target (or oligonucleotide) while the other is attached to the solid support. However, if a specific RNA or DNA binding protein is used, it is preferable to attach the protein to the solid support while the specific sequence motif that the protein binds can be incorporated during synthesis at any convenient position in the sequence of the RNA target or oligonucleotide. Finally, attachment of the protein to solid support can be omitted if adsorption to nitrocellulose filters is used instead (as described above).

4. High-throughput Assays Using Fluorescence Energy Transfer (FET).

Fluorophores such as fluorescein, rhodamine and coumarin have distinctive excitation and emission spectra. Fluorescence energy transfer occurs between pairs of fluorophores in which the emission spectrum of one (donor) overlaps the excitation spectrum of the other (acceptor). For appropriately chosen pairs of fluorescent molecules, emission by the donor probe is reduced by the presence of an acceptor probe in. close proximity because of direct energy transfer from the donor to acceptor. Thus, upon excitation at a wavelength absorbed by the donor probe, a reduction in donor emission and increase in acceptor emission relative to the probes alone is observed if the probes are close in space. In other words, the donor's emission fluorescence is quenched by the acceptor, which in turn emits a higher wavelength fluorescence. FET, however, is effective only when donor and acceptor are in close proximity. The efficiency of energy transfer is inversely proportional to the sixth power of the distance between the donor and acceptor probes, thus the extent of these effects can be used to calculate the distance separating the probes. FET has been used to probe the structure of transfer RNA molecules (Beardsley et al., *Proc.Natl.Acad.Sci.USA* 65:39, 1970), as well as for detection of hybridization, for restriction enzyme assays, for DNA-unwinding assays, and for other applications).

A. Intramolecular FET

Figure 3:
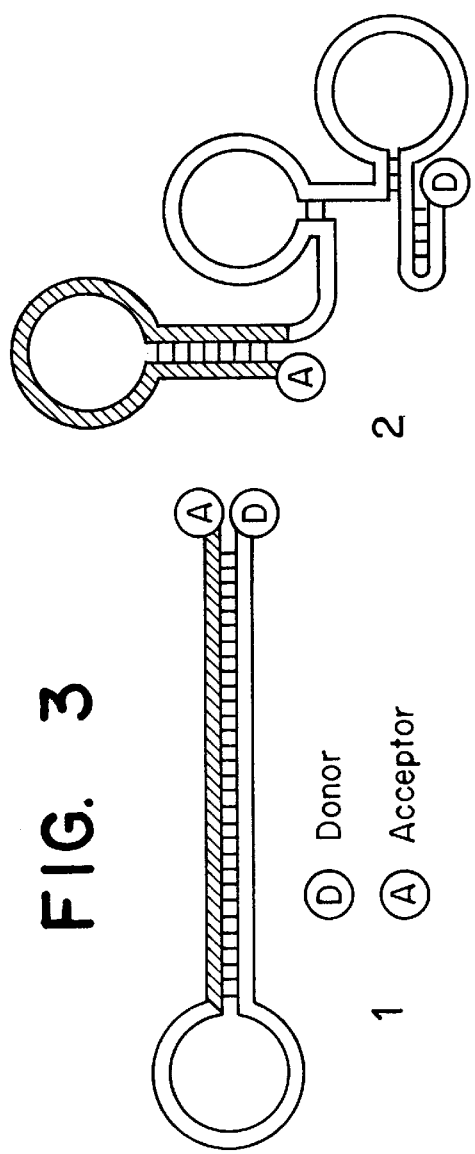
FIG. 3 is a graphic illustration of different conformations of a model target RNA.

FET is used in the present invention to monitor a change in target RNA conformation, when the distance between the donor and acceptor probes differs significantly between the different conformations. In one embodiment an RNA molecule is used in which an internal hybridization probe sequence has been engineered as in, for example, FIG. 3. The solid region represents target RNA sequences and the hatched region represents an internal probe sequence that is complementary to a large portion of the target sequence. In conformation 1, the probe and target sequences hybridize, bringing the acceptor (A) and donor (D) fluorescent probes into close proximity. In the presence of a ligand that binds to a structured conformation of the target sequences, conformation 2 is stabilized; as a consequence, the probes are further apart. A predominance of conformation 2 is reflected in a relative increase in donor fluorescence and/or a decrease in acceptor fluorescence.

B. Use of oligonucleotide hybridization and FET

Figure 4:
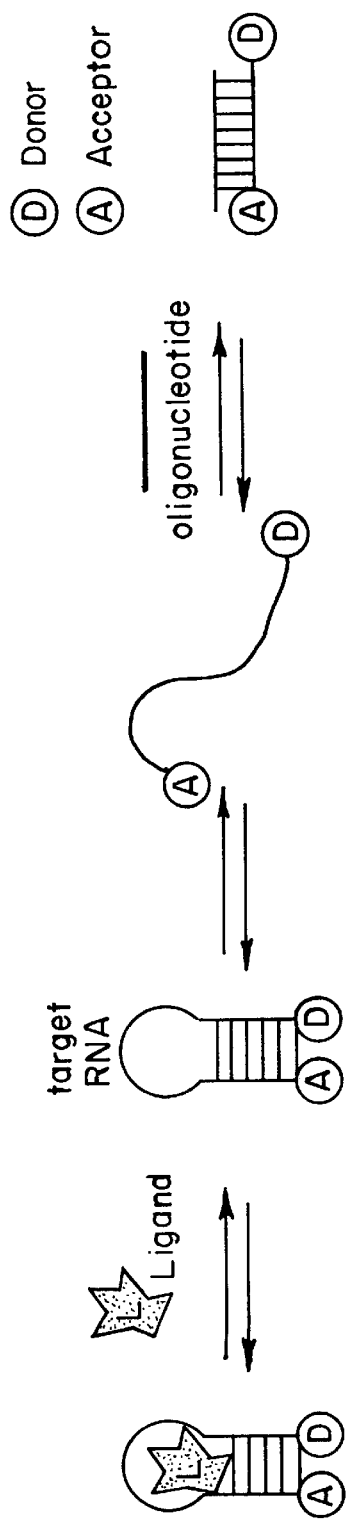
FIG. 4 is a graphic illustration of the use of intramolecular fluorescence energy transfer to monitor RNA structure.

Acceptor and donor in the same strand: In this embodiment, the target RNA is designed so that the 5'- and 3'- ends of the RNA stay in close proximity when folded, allowing FET. FIG. 4 shows the model in which the formation of hybrids with another DNA or RNA oligonucleotide will result in a decrease in the FET efficiency due to the larger distance between donor and acceptor.

Acceptor and donor in separate strands: This approach is useful when the design of the RNA target does not allow the incorporation of both donor and acceptor fluorophores in the same strand. In this case, the donor and acceptor are in separate strands and come in close proximity in the target:oligonucleotide hybrid (FIG. 5). In this embodiment, the formation of the hybrid results in an increase of FET.

5. High-throughput Assays Using Conformation-specific Nucleases

In practicing the present invention the ligand-induced stabilization of a folded conformation of a target RNA by binding decreases the fraction of the target RNA present in an unfolded conformation. Conversely, in the absence of ligand, a greater fraction of the RNA is found in the unfolded state than in the presence of such a compound. Folded conformations of RNA are characterized by double-stranded regions in which base pairing between RNA strands occurs. A variety of nucleolytic enzymes, such as S1 and mung bean nucleases, preferentially digest phosphodiester bonds in single-stranded RNA relative to double stranded RNA. Such enzymes can be used to probe the conformation of RNA target molecules in the current invention.

In a typical assay, target RNA and test compound(s) are preincubated to allow binding to occur. Next, an appropriate nuclease is added, and the mixture is incubated under appropriate conditions of temperature, nuclease concentration, ionic strength and denaturant concentration to ensure that (in the absence of ligand) about 75% of the RNA is digested according to the specificity of the nuclease used, within a short incubation period (typically 30 minutes). The extent of digestion is then measured using any method well-known in the art for distinguishing between free ribonucleoside monophosphates and oligonucleotides, including, without limitation, acid precipitation and detection of labelled RNA, FET of RNA containing donor and acceptor fluorescence probes, and electrophoretic separation and detection of RNA by autoradiography, fluorescence, UV absorbance, hybridization with labeled nucleic acid probe or dye binding.

Figure 6:
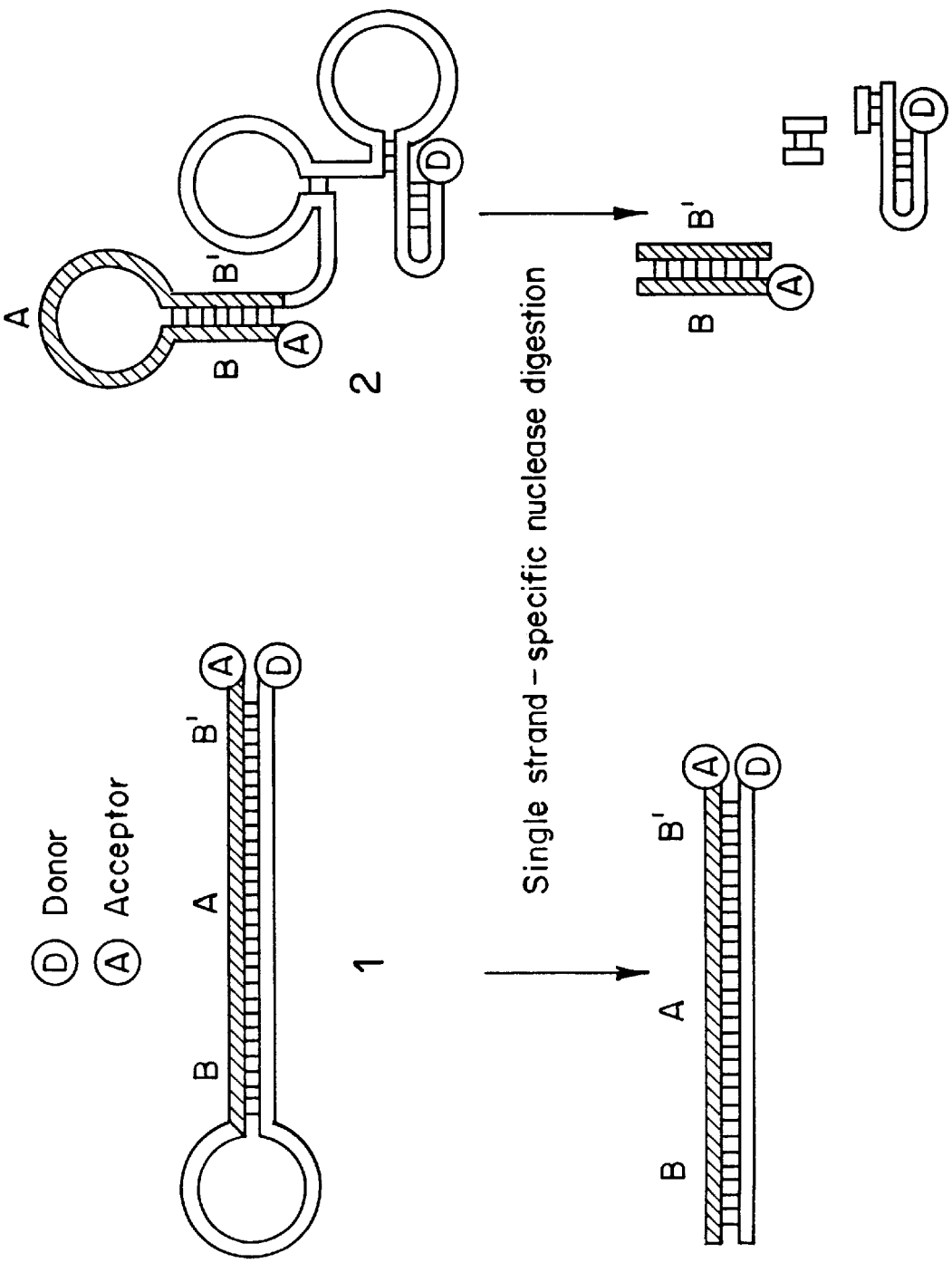
FIG. 6 is a graphic illustration of the effect of nuclease digestion on alternative target RNA conformations.

Changes in conformation between two or more alternative folded RNA conformations can also be detected using nuclease digestion. In this embodiment, each of the conformations typically contains some regions of double stranded RNA. If the alternate conformations involve differing amounts of double-stranded regions, they can be distinguished by measuring the amount of nuclease-resistant material. If the overall double-stranded content of these structures is comparable, it is necessary to distinguish between the nuclease-resistant fragments yielded by nuclease digestion of different target RNA conformations. FIG. 6 illustrates the effect of single-strand specific nuclease digestion of two alternate target RNA conformations that yields stable products differing in size and sequence content. For example, although regions B and B' are found among the nuclease resistant fragments of both conformations 1 and 2, region A is not found after digestion of conformation 2.

Specific RNA fragments may be detected and quantified by any method well-known in the art, including, without limitation, labelling of target RNA, hybridization with target-specific probes, amplification using target-specific primers and reverse-transcriptase-coupled PCR, and size determination of digestion products (if digestion products of a specific RNA conformation have characteristic sizes that distinguish them from the digestion products of other conformations).

Nucleases that are specific for different nucleic acid structures may also be used to quantify hybridization of complementary oligonucleotides.

Figure 7:
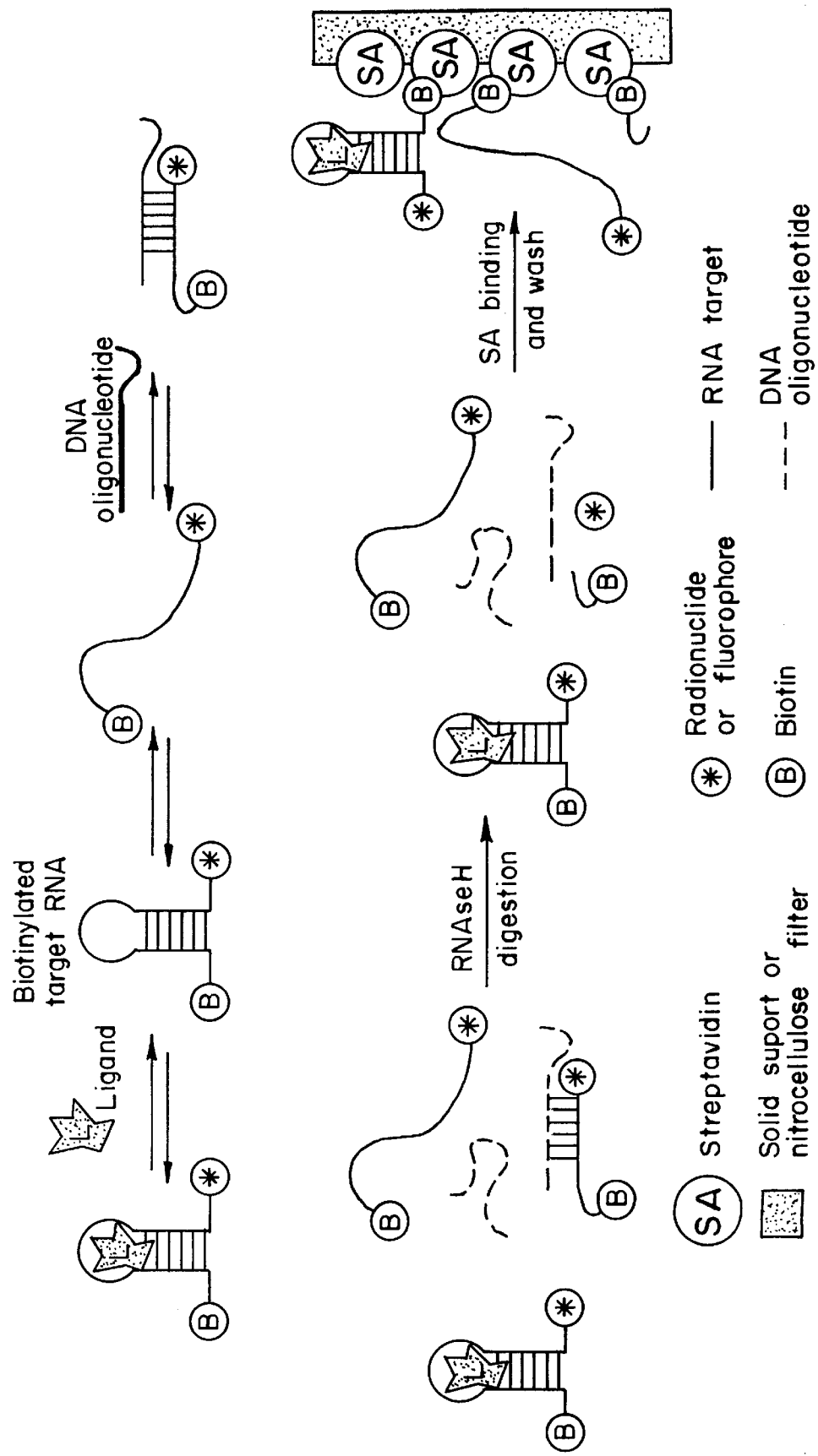
FIG. 7 is a graphic illustration of the use of RNAase H digestion, in conjunction with biotinylated and labelled target RNA to measure RNA:DNA hybrids.

RNAse H: RNAse H is a commercially available nuclease that specifically degrades the RNA strand of RNA:DNA hybrids. A 5'-end or 3'-end biotinylated RNA target is also labeled at the other end with a radionuclide or a fluorophore such as fluorescein, rhodamine or coumarin. RNAase H digestion of the RNA:DNA hybrids formed during the reaction results in physical separation of the biotin moiety (on one end) from the fluorophore or radionuclide (on the other end) (FIG. 7). RNA target strands not involved in hybrid formation will not be digested by RNAse H and can be quantified after streptavidin binding as described above. In this embodiment, the signal obtained will increase if the test ligand binds the target RNA.

Figure 8:
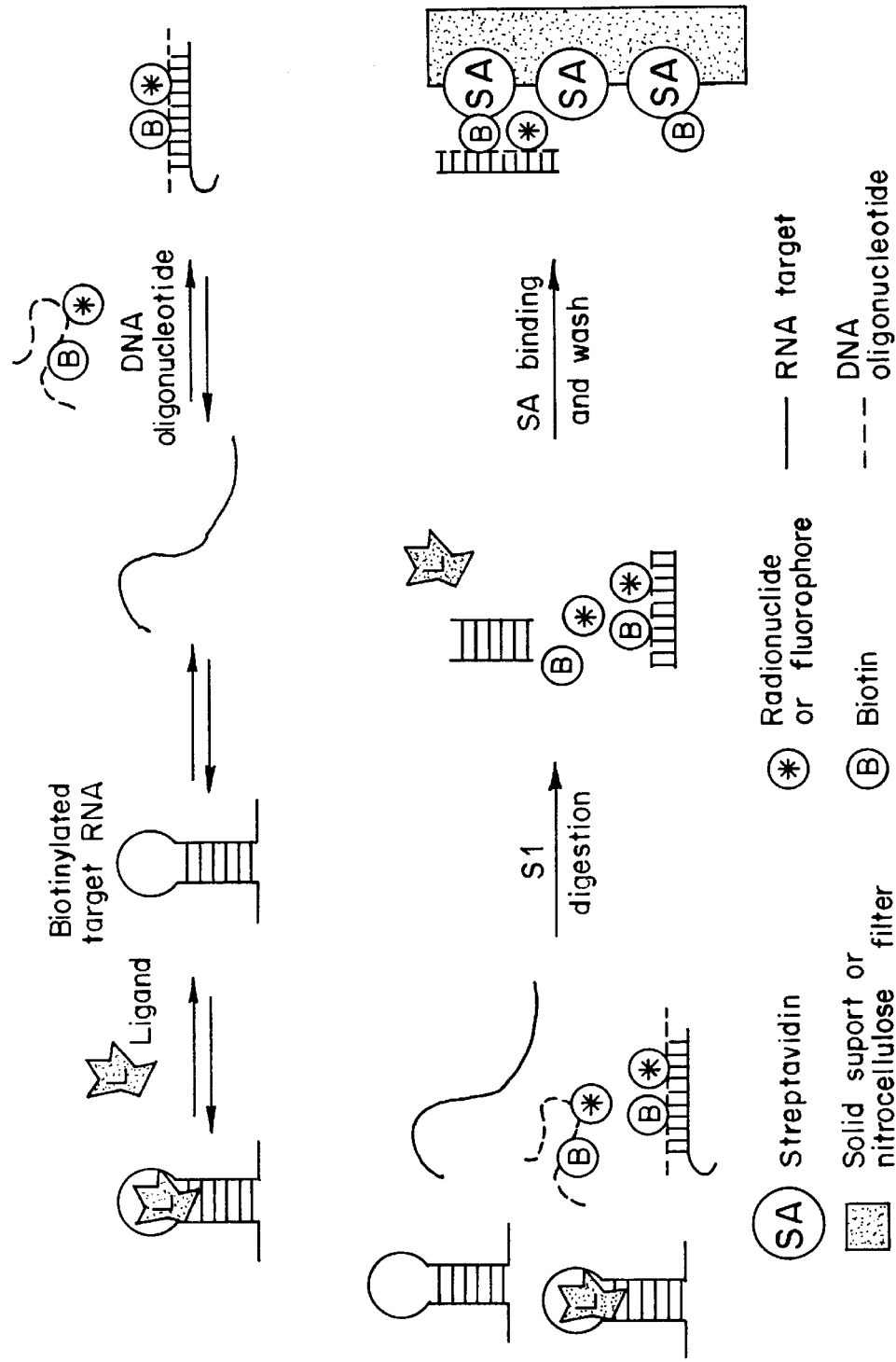
FIG. 8 is a graphic illustration of the use of S1 nuclease, in conjunction with a biotinylated and labelled oligonucleotide, to measure RNA:DNA hybrids.

Nuclease S1: Single stranded nucleic acids can be specifically digested with the commercially available nuclease S1 (Promega, Madison, Wis.). This enzyme can be used in the present invention if the DNA oligonucleotide carries the biotin moiety as well as the label at an internal position (FIG. 8). Labelled strands forming hybrids resist digestion by S1 nuclease and are quantified by SA-mediated capture as described above. The label can also be in the section of RNA that participates in hybrid formation. Alternatively, the same approach can be carried out with single strand specific RNases such as RNAse T1 or RNAase ONE™ (Promega), in which case the label must be located in the RNA target.

6. Conformation Specific Binding.

A variety of materials bind with greater affinity to one or another type of RNA structure. A prime example of this phenomenon is hydroxyapatite, which has greater affinity for double-stranded than for single-stranded nucleic acids. Nitrocellulose, by contrast, has higher affinity for single-stranded than for double-stranded RNA. These and other similar materials can be used to distinguish between different conformations of RNA, particularly where ligand binding stabilizes one conformation that differs significantly from other conformations in its single-stranded content. These methods are generally useful when ligand binding stabilizes folded RNA conformations relative to the unfolded state.

Antibodies that recognize RNA may also be used in a high-throughput mode to identify ligands according to the present invention. Useful antibodies may recognize specific RNA sequences (and/or conformations of such sequences) (Deutscher et al., *Proc.Natl.Acad.Sci.USA* 85:3299, 1988), may bind to double-stranded or single-stranded RNA in a sequence-independent manner (Schonborn et al., *Nuc.Acids Res.* 19:2993, 1991), or may bind DNA:RNA hybrids specifically (Stumph et al., *Biochem.* 17:5791, 1978). In these embodiments, binding of antibodies to the target RNA is measured in the presence and absence of test ligands.

7. Biophysical Measurements.

A variety of biophysical measurements can be used to examine the folded and unfolded conformation(s) of RNA molecules and detect the relative amounts of such conformations, including, without limitation, UV absorbance, CD spectrum, intrinsic fluorescence, fluorescence of extrinsic covalent or noncovalent probes, sedimentation rate, and viscosity. Each of these properties may change with changing RNA conformation. In these embodiments, measurements are performed on mixtures of target RNA and appropriate buffer, salt and denaturants in the presence and absence of test ligand(s). A change in a measurable property, particularly one that suggests conversion of unfolded to folded forms of the RNA, is indicative of ligand binding.

8. Changes in Conformational Stability.

Any of the structural measurements described above can be used to examine the stabilization of a conformation by ligand binding. The stability of such a conformation is defined as the free energy difference between that conformation and alternative (typically unfolded) conformations. Conformational stability can be measured under constant conditions, with and without test ligand(s), or over a range of conditions. For example, the effect of increasing temperature on structure, as measured by one of the methods above, can be measured in the presence and absence (control) of test ligand(s). An increase in the temperature at which structure is lost is indicative of ligand binding.

9. Disruption of Protein Binding to Adjacent RNA.

A variety of proteins are known that bind to specific RNA sequences in a manner that is dependent on the three-dimensional structure of the RNA. In these embodiments, protein binding is used as a probe of RNA structure and its alteration upon ligand binding. A target RNA sequence and an RNA sequence to which a protein binds are incorporated within the same RNA molecule. The interaction of a binding protein with its binding sequence is measured in the presence and absence of test ligands. Ligand-induced changes in the RNA conformation that alter the conformation of the protein binding site are detected by measurement of protein binding.

Applications

Binding to a given target RNA is a prerequisite for pharmaceuticals intended to modify directly the action of that RNA. Thus, if a test ligand is shown, through use of the present method, to bind an RNA that reflects or affects the etiology of a condition, it may indicate the potential ability of the test ligand to alter RNA function and to be an effective pharmaceutical or lead compound for the development of such a pharmaceutical. Alternatively, the ligand may serve as the basis for the construction of hybrid compounds containing an additional component that has the potential to alter the RNA's function. In this case, binding of the ligand to the target RNA serves to anchor or orient the additional component so as to effectuate its pharmaceutical effects. The fact that the present method is based on physico-chemical properties common to most RNAs gives it widespread application. The present invention can be applied to large-scale systematic high-throughput procedures that allow a cost-effective screening of many thousands of test ligands. Once a ligand has been identified by the methods of the present invention, it can be further analyzed in more detail using known methods specific to the particular target RNA used. For example, the ligand can be tested for binding to the target RNA directly, such as, for example, by incubating radiolabelled ligand with unlabelled target, and then separating RNA-bound and unbound ligand. Furthermore, the ligand can be tested for its ability to influence, either positively or negatively, a known biological activity of the target RNA.

Non-Limiting examples of RNA targets to which the present invention can applied are shown in the following table:

| Therapeutic Area | RNA Targets |
| --- | --- |
| Antivirals | HBV epsilon sequence; HCV 5' untranslated region; HIV packaging sequence, RRE, TAR; picornavirus internal translation enhancer |
| Antibacterials | RNAse P, tRNA, rRNA (16S and 23S), 4.5S RNA |
| Antifungals | Similar RNA targets as for antibacterials |
| Rheumatoid Arthritis | Alternative splicing of CD23 |
| Cancer | Metastatic behavior is conferred by alternatively-spliced CD44; mRNAs encode proto-oncogenes |
| CNS | RNA editing alters glutamate receptor-B, changing calcium ion permeability |
| Neurofibromatosis type I | RNA editing introduces stop codon at 5' end of NF1 GAP-related domain to inactivate NF1 epigenetically |
| Cardiovascular | RNA editing influences amount of ApoB-100, strongly associated with atherosclerosis |

The following examples are intended to further illustrate the invention without limiting it thereof.

EXAMPLE 1

DETECTION OF RNA FOLDING USING A GEL SHIFT ASSAY

A. Rationale

Figure 9:
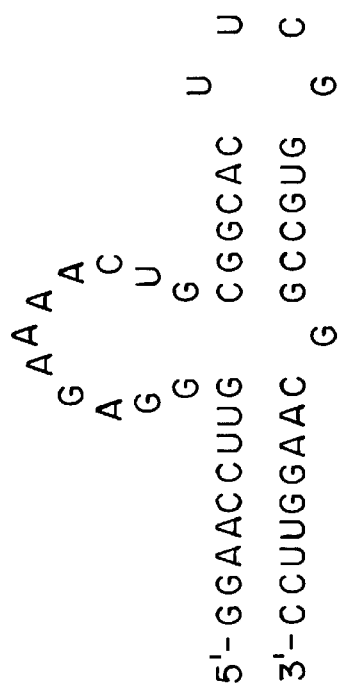
FIG. 9 is a graphic illustration of the structure of AB-RNA (top) and of he reaction of AB-RNA with either ATP or with a complementary oligonucleotide bottom).
Figure 9:
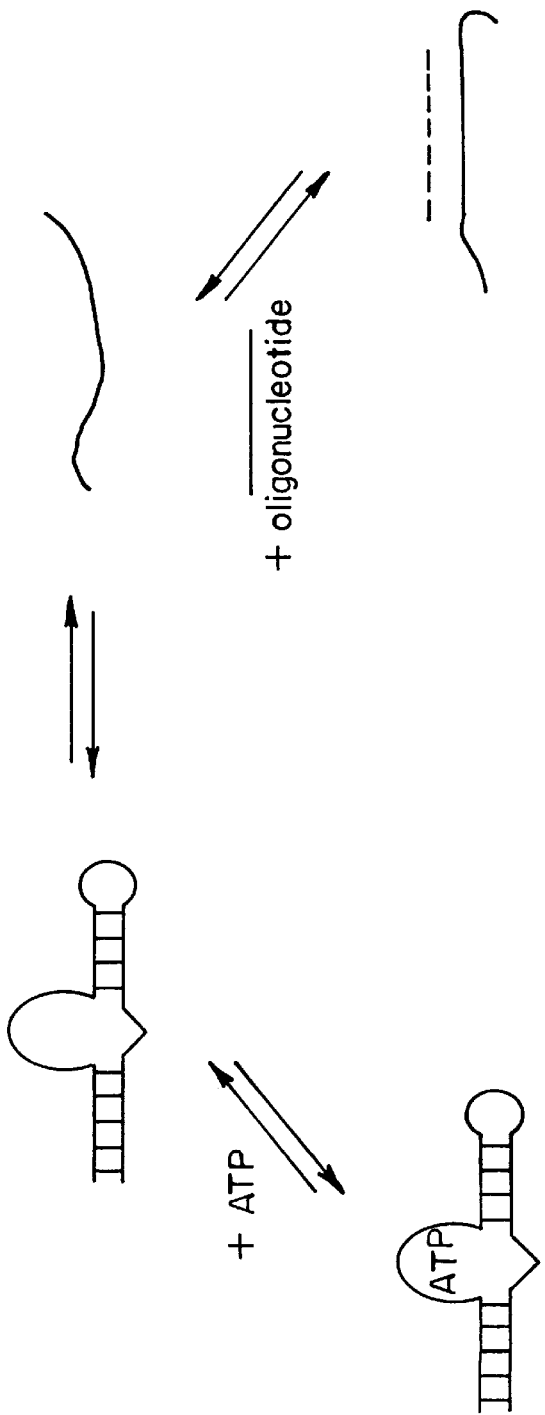

The RNA molecule shown in FIG. 9 (top), designated AB-RNA, was shown to bind ATP with high affinity (Sassanfor et al., *Nature*, 364:550, 1993). In the experiments described below, this RNA was used to illustrate different embodiments of the present invention.

As depicted in FIG. 9 (bottom), in practicing the present invention, incubation of this RNA (AB-RNA) with ATP and a competitor oligonucleotide allows the formation of an ATP:AB-RNA complex as well as an oligo:AB-RNA hybrid. In the absence of ATP, formation of the hybrid is favored. By contrast, in the presence of ATP, the formation of the hybrid is less favored due to the formation of a stable ATP:RNA complex. Thus, measurement of the amount of oligonucleotide:RNA hybrids in the reaction mixture indicates the presence or absence of an RNA-binding ligand.

B. Methods

AB-RNA was transcribed using as template the DNA oligonucleotide RBS-87-8A, (5'-GGAAC CTTGC CGGCA CCGAA GTGCC GCAGT TTCTT CCCAA GGTTC CTATA GTGAG TCGTA TTA-3'SEQ ID NO: 1), which contains the sequence for the T7-RNA polymerase promoter followed by a region encoding AB-RNA. [$^{32}$P]-labelled AB-RNA was obtained by including [$^{32}$P]-UTP in the transcription reaction. Conditions for the T7 RNA polymerase transcription reaction using oligonucleotide templates have been described by Milligan et al., *Nuc. Acids Res.*, 15:8783, 1987.

[$^{32}$P]-labelled AB-RNA (approx. 30,000 cpm) in a 360 µl mixture containing 37.5 mM Tris pH 7.5, 150 mM NaCl and 7.5 mM MgCl$_2$ was heat denatured at 90° C. for 2 min and then chilled on ice for 2 min. The mixture was split into three 120 µl aliquots which were supplemented with 20 µl of water, 300 µM ATP, or 300 µM UTP. Nine 12 µl aliquots of each of these mixtures were then supplemented with varying amounts of the complementary RBS-87-8A oligonucleotide and water so that the final volume of each was 20 µl. The resulting reaction mixtures contained final oligonucleotide concentrations ranging from 0 to 1.97 μM and either one of 30 μM ATP, 30 μM UTP, or no ligand. The reaction mixtures were then supplemented with 3 μl of loading dye and loaded onto a 12% polyacrylamide native gel. The gel and running buffers contained 1×TBE buffer in addition to 37.5 mM Tris pH 7.5, 150 mM NaCl,7.5 mM $MgCl_2$ and the corresponding ligand concentration.

C. Results

Figure 10:
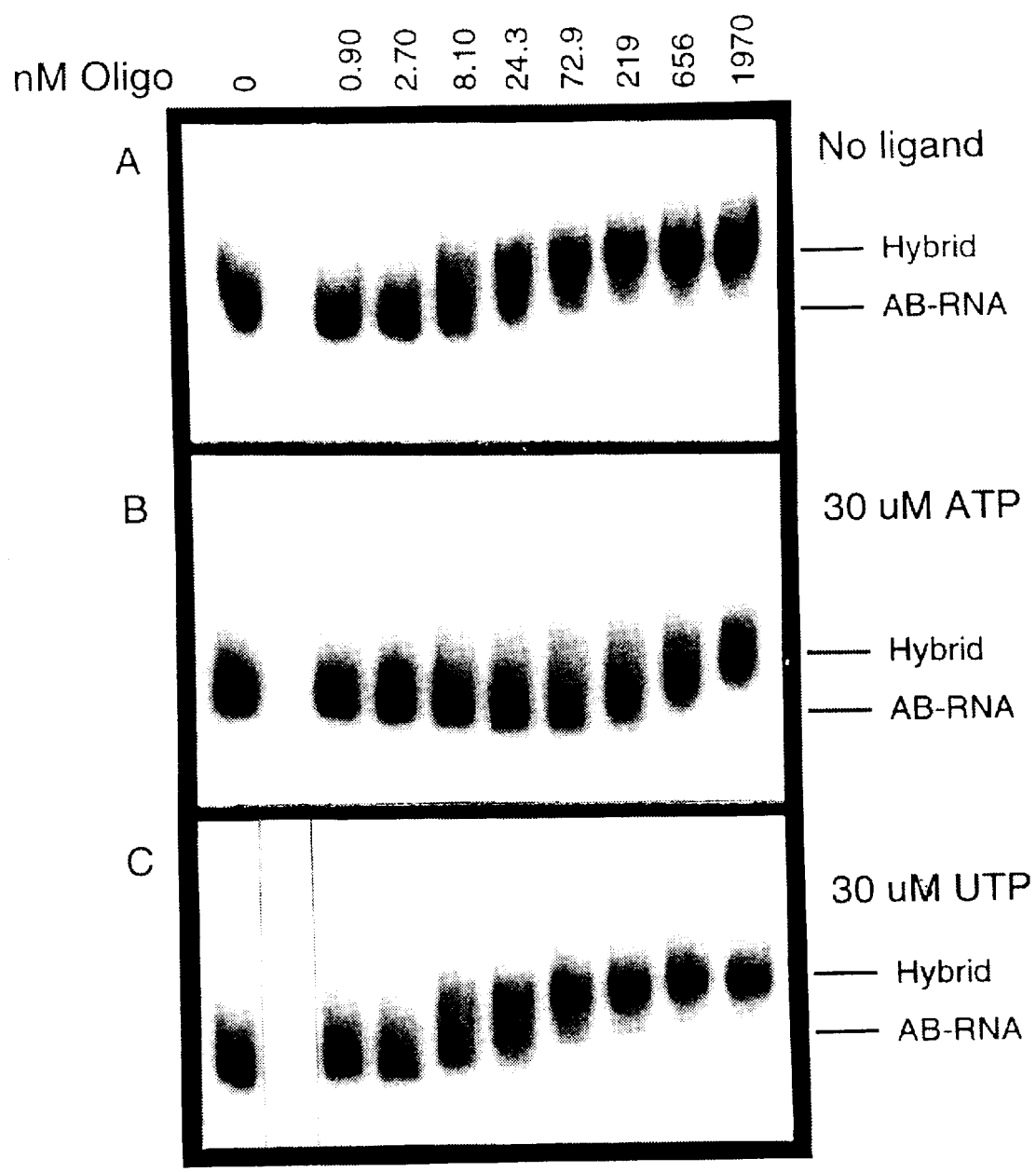
FIG. 10 depicts an autoradiogram of a native polyacrylamide gel in showing the effect of ATP and UTP on the hybridization of radiolabelled AB-RNA to a complementary DNA oligonucleotide.

Resolution of hybridized and unhybridized RNA by gel electrophoresis indicated that the conversion of 50% of the AB-RNA into the RNA:DNA hybrid requires approximately 24 nM RBS-87-8A oligonucleotide in the absence of ligand, and conversion of 100% requires at least 72.9 nM oligonucleotide (FIG. 10, top panel). In contrast, in presence of 30 μM ATP, 656 nM to 1970 nM RBS-87-8A oligonucleotide concentrations were required to induce the formation of a similar amount of hybrids (FIG. 10, middle panel). This effect is the result of competition between ATP and the oligonucleotide for binding to the AB-RNA. Furthermore, this experiment shows that UTP is unable to compete with the oligonucleotide, demonstrating that the observed effect is ligand-specific (FIG. 10, bottom panel).

EXAMPLE 2

HIGH-THROUGHPUT DETECTION OF RNA LIGANDS USING STREPTAVIDIN-COATED PARAMAGNETIC BEADS

A. Methods

The [$^{32}$P]-labelled ATP-binding RNA described in Example 1 above (AB-RNA) was heat denatured at 90° C. for 2 min in binding buffer (50 mM Tris pH 7.5, 200 mM NaCl, and 10 mM $MgCl_2$) and chilled on ice for 2 min. 37.5 μl aliquots of the heat denatured AB-RNA were then mixed with 12.5 μl of a solution containing 12.5 pmol of the 5'-biotinylated oligonucleotide RBS-96-60 (having a nucleotide sequence identical to RBS-87-8A described in Example 1 above) and varying amounts of ATP or UTP. After a brief incubation at room temperature, the mixture was transferred into 96-well plates containing 0.5 mg paramagnetic beads coated with streptavidin (PMP-SA) (Promega, Madison, Wis.). Plates were incubated at room temperature for 15 min to allow binding. A strong magnet was placed under the plate, after which the PMP-SA beads were washed with 50 μl of binding buffer. [$^{32}$P]-labelled AB-RNA bound to the beads was then quantitated by Cerenkov counting in a Microbetta LSC-counter (Wallac).

B. Results

Figure 11:
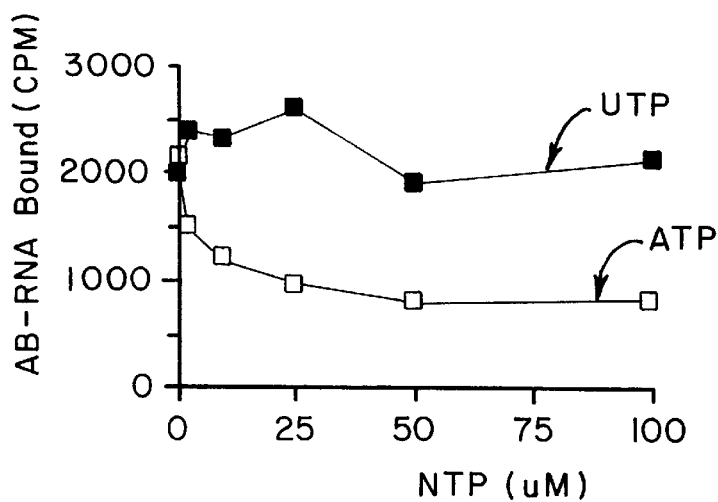
FIG. 11 is a graphic illustration of the effect of ATP and UTP on the binding of AB-RNA:biotinylated DNA hybrids to streptavidine-coated paramagnetic beads.

FIG. 11 shows the amounts of [$^{32}$P]-AB-RNA bound to the PMP-SA beads in the presence of increasing concentrations of either ATP or UTP, representing the hybrids formed between the biotinylated oligonucleotide (RBS-96-60) and the target RNA (AB-RNA). The results show that the amount of hybrids formed can be reduced by 50% by adding as little as 25 μM ATP. As expected, no effect was seen when UTP was used as the ligand.

EXAMPLE 3

HIGH-THROUGHPUT DETECTION OF RNA LIGANDS USING NITROCELLULOSE FILTER BINDING

A. Rationale:

This embodiment of the present invention takes advantage of the fact that most proteins adsorb tightly to nitrocellulose filters. When a biotinylated oligonucleotide and a labelled target RNA are used (as described in Example 2 above), free streptavidin (SA) or a SA derivative is added to the reaction to allow binding to the biotin moiety in the oligonucleotide, after which the reaction is filtered through 96-well nitrocellulose filter plates. In this way, labelled target RNA hybridized to the biotinylated oligonucleotide is retained in the filter, while non-hybridized RNA is lost.

B. Method:

The target RNA was an RNA molecule containing the binding site for the HIV Rev protein (Rev Responsive Element, RRE; 5'-GAAUA CUAUG GGCGC AGCGU CAAUG ACGCU GACGG UACAG GCCAG ACAAU UAUUG UCUGG UAUAG U-3' SEQ ID NO: 2) which had been labelled with $^{32}$P as described in Example 1 above. The biotinylated oligonucleotide, designated RBS-79-91b-B, is complementary to positions 5 thru 28 of the RRE target RNA and has the sequence 5'-biotin-CGTCA TTGAC GCTGC GCCCA TAGTG C-3' SEQ ID NO: 3. 0.1 pmol of [$^{32}$P]-RRE RNA were incubated with 5 pmol of RBS-79-91b-B in 40 μl of buffer containing 50 mM Tris pH 7.5 and 50 mM NaCl. After 15 min at room temperature, varying amounts of streptavidin alone (SA), streptavidin conjugated to β-galactosidase (SA:BG), or streptavidin conjugated to alkaline phosphatase (SA:AP) were added to the mixture and allowed to bind for 20 min before filtration through Millipore HATF nitrocellulose filter plates. The filtrate was further washed with 400 μl of the same buffer and the amount of RRE retained in the filter was determined by liquid scintillation counting.

C. Results

Figure 12:
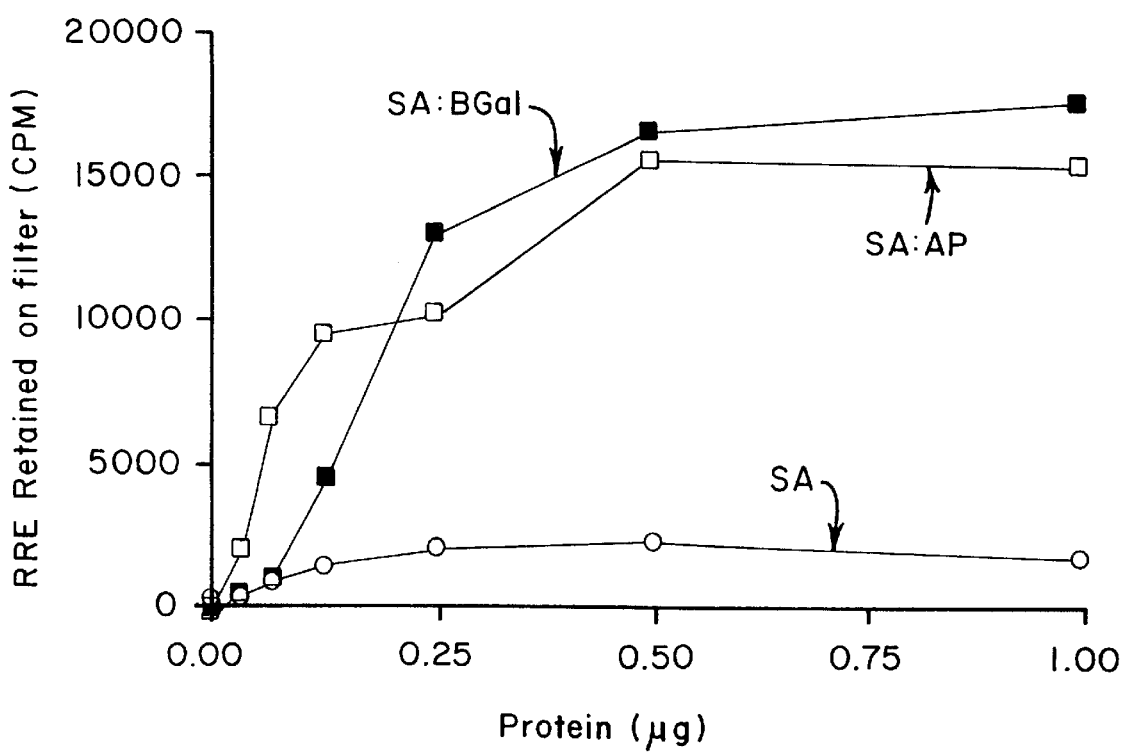
FIG. 12 is a graphic illustration of the effect of adding increasing amounts of streptavidin (SA), streptavidin-alkaline phosphatase (SA:AP), or streptavidin-beta galactosidase (SA:BG) on the binding to nitrocellulose filters of hybrids between radiolabelled RRE RNA and a biotinylated complementary DNA oligonucleotide.

FIG. 12 shows that SA-conjugated proteins increase the efficiency of retention of labelled RNA:oligonucleotide hybrids. If an RRE-specific ligand is included in the reaction, the relative amount of labelled RRE RNA bound to the filters should decrease.

EXAMPLE 4

CHARACTERIZATION OF NITROCELLULOSE FILTER BINDING ASSAY

The following experiments were performed to determine the effect of various experimental parameters on the high-throughput assay described in Example 3 above.

It was first determined that 2 μg of SAAP, with a free biotin binding activity of 20 pMol/μg of protein, is sufficient to ensure quantitative retention of hybrids on NC-filters.

Figure 13A:
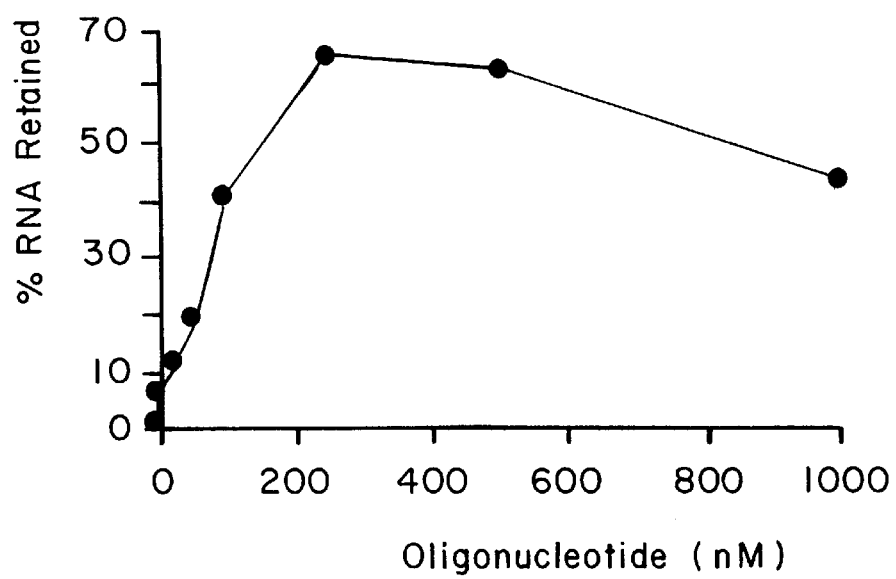
FIG. 13A is a graphic illustration of the effect of adding increasing concentrations of oligonucleotide 91B on the binding to nitrocellulose filters of hybrids between radiolabelled AB RNA and biotinylated complementary 91B oligonucleotide.

It was then determined that, typically, a two-fold molar excess of oligonucleotide over the RNA target is sufficient to achieve substantial hybrid formation. A titration of the biotinylated oligonucleotide 67B in a 30 min SCAN reaction containing 100 nM radiolabeled AB-RNA, 50 mM Tris pH 7.5, 200 mM NaCl, and 10 mM $MgCl_2$ is shown in FIG. 13A. Addition of the oligonucleotide at concentrations above 500 nM resulted in a gradual loss of retention, suggesting that the capacity of the SAAP is saturated. The ability to use minimal amounts of oligonucleotides decreases the amount of SAAP required for quantitative NC-filter retention and therefore reduces the cost of the assay.

Figure 13B:
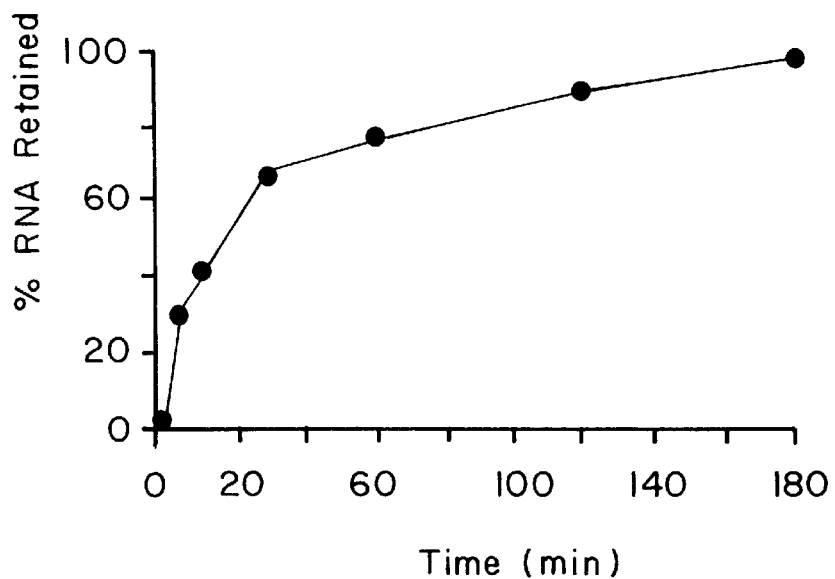
FIG. 13B is a graphic illustration of the time course of the formation of hybrids between radiolabelled AB RNA and biotinylated complementary 91B oligonucleotide.

FIG. 13B shows a time course for reactions which contain 250 nM oligonucleotide. The results indicate that this amount of oligonucleotide (2.5-fold molar excess over RNA target) is sufficient to mediate the quantitatively retention of hybrids on the filter, even when the SCAN reaction goes to completion.

Figure 13C:
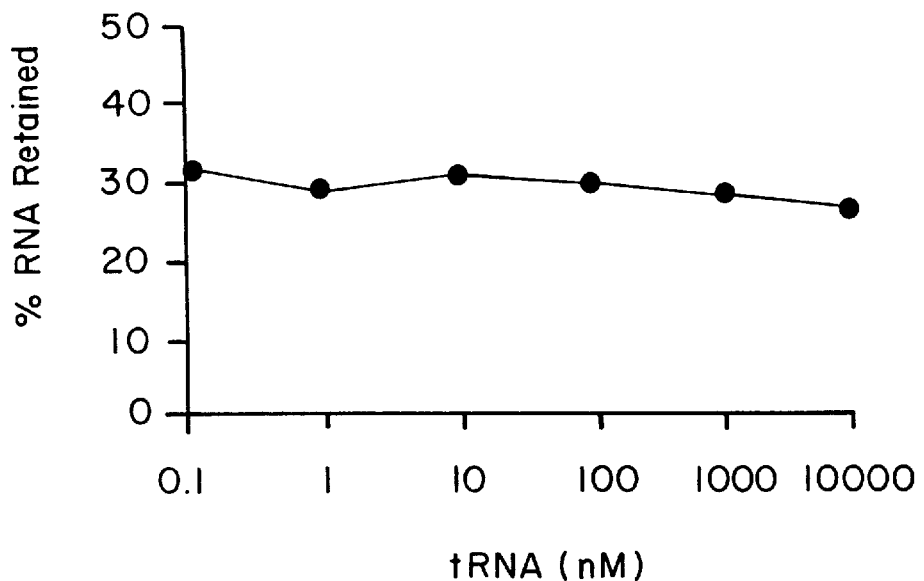
FIG. 13C is a graphic illustration of the lack of effect of adding increasing concentrations of tRNA on the formation of hybrids between radiolabelled AB RNA and biotinylated complementary 91B oligonucleotide.

FIG. 13C shows 10-minute SCAN reactions in which increasing concentrations of yeast tRNA have been added as a non-specific competitor. The results show that even a 100-fold molar excess of yeast tRNA did not affect the retention of hybrids on nitrocellulose filters. The addition of a large excess of a non-specific RNA competitor to SCAN assays is expected to reduce the incidence of unwanted positive screening results caused by ligands that interact non-specifically with nucleic acids.

Figure 13D:
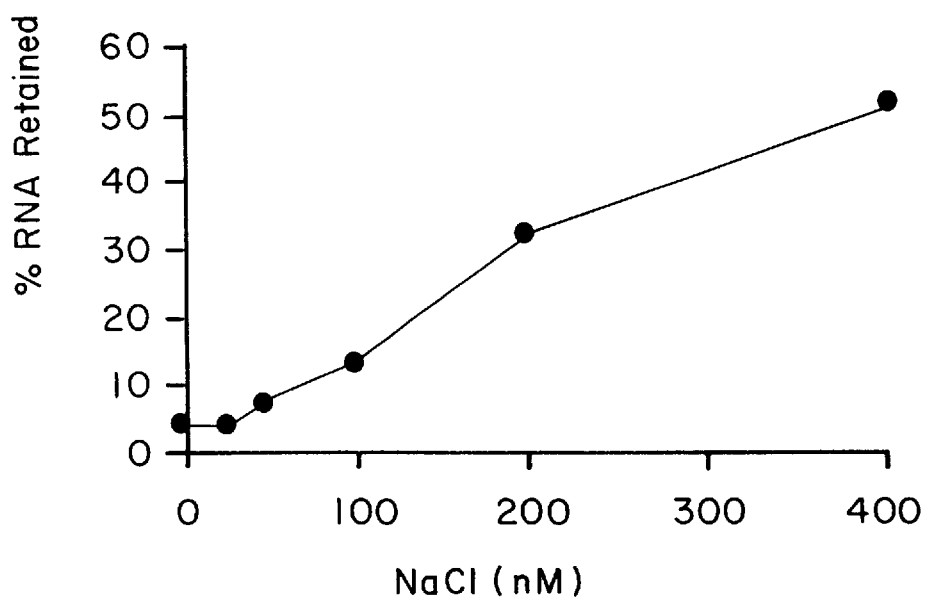
FIG. 13D is a graphic illustration of the effect of adding increasing concentrations of sodium chloride on the formation of hybrids between radiolabelled AB RNA and biotinylated complementary 91B oligonucleotide.

FIG. 13D illustrates the effect of NaCl (in absence of $MgCl_2$) under the same conditions. As expected, the formation of hybrids is stimulated by the addition of NaCl. Interestingly, in presence of 10 mM $MgCl_2$, no NaCl was required to obtain efficient retention. Thus, hybridization rates show dependence on ionic strength. Additional experiments indicated that the ionic strength dependence varied according to the RNA-target and oligonucleotide being used.

Similar results were obtained in SCAN reactions using other RNA targets, including HIV RRE and TAR elements. By varying parameters such as ionic strength, oligonucleotide concentration and design, and target-RNA concentration, it was possible to modulate the hybridization kinetics in order to achieve a suitable extent of hybrid formation in a time appropriate for high- throughput screening, i.e., at room temperature, 30–50% retention in reactions containing 10–100 nM RNA target and 2–4-fold molar excess of biotinylated oligonucleotide over the target RNA in reaction times of 0.5 to 2 hours.

EXAMPLE 5

PARAMETERS FOR THE DESIGN OF OLIGONUCLEOTIDES FOR USE IN SCAN REACTIONS

Figure 14A:
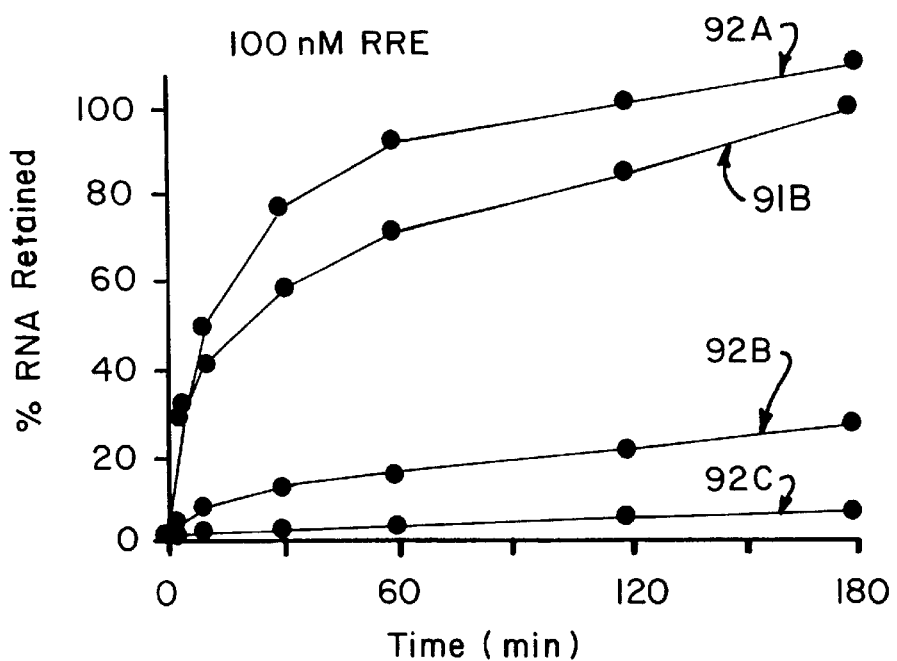
FIG. 14A is a graphic illustration of the time course of hybrid formation between radiolabelled HIV RRE RNA and biotinylated oligonucleotides, using 100 nM target RNA and 250 nM oligonucleotide.

The experiments described below were performed to identify optimal oligonucleotide structures for use in high-throughput SCAN reactions. The RNA target was a radiolabeled fragment of the HIV Rev response element (RRE) containing the high affinity binding site for Rev protein. It was hypothesized that the region including positions 9–12 of the RNA target (see FIG. 14C) may have a higher probability to unfold and may therefore provide a preferred site of entry (nucleation site) for oligonucleotide binding. Therefore, various oligonucleotides with full or partial complementarity to this region were tested in the reaction.

In order to avoid differences due to accessibility of the biotin moiety in the hybrids, all oligonucleotides used in this series had identical 5'-biotinylated ends while their 3'-ends varied in length. The full length of each oligonucleotide was complementary to the corresponding region of the RNA target (shown in uppercase in FIG. 14C). The full length of the RNA-target used in all reactions is shown to the far left in FIG. 6C while the regions of RNA complementary to oligonucleotides 92A, 99A, 92B and 92C are shown on partial structures.

Figure 14B:
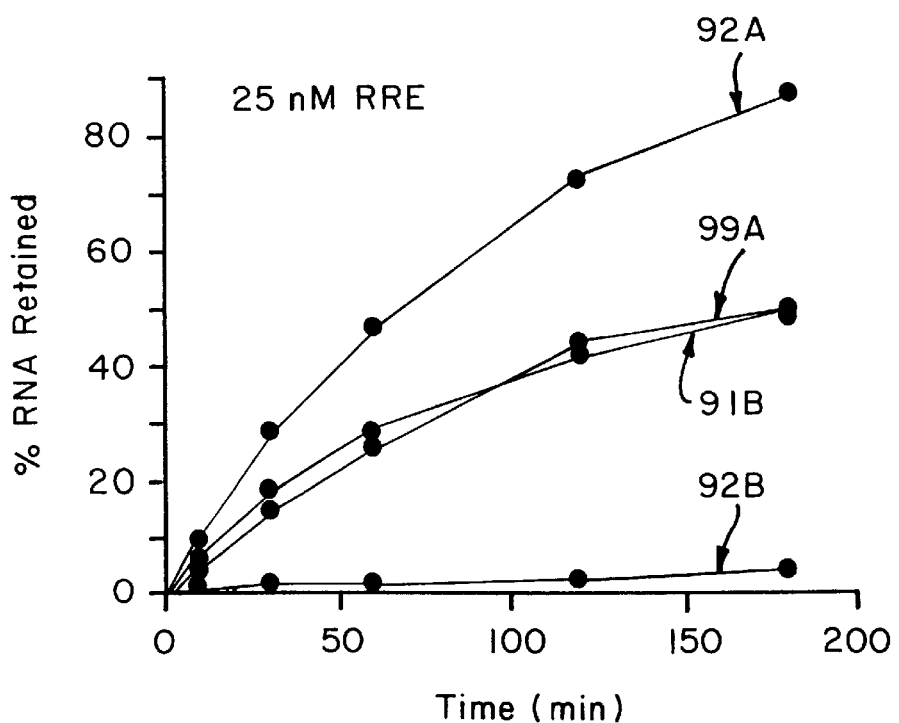
FIG. 14B is a graphic illustration of the time course of hybrid formation between radiolabelled HIV RRE RNA and biotinylated oligonucleotides, using 25 nM target RNA and 50 nM oligonucleotide.

Time course reactions containing 100 nM radiolabeled RNA-target and 250 nM oligonucleotide (FIG. 14A), or 25 nM radiolabeled RNA-target and 50 nM oligonucleotide (FIG. 14B) evidenced dramatic differences in hybrid formation. Comparison of the reactions containing oligonucleotides 91B, 99A and 92A indicated that, contrary to expectation, a longer oligonucleotide will not necessarily show faster kinetics. Instead, the results indicate that the positioning of the 3' terminus of the oligonucleotide, and the number of complementary bases within the region 9–12, both play a dominant role in determining hybrid formation rates. Most dramatic is the difference between oligonucleotides 92A, 99A, and 92B, whose lengths differ by one base at their 3' termini.

These observations are consistent with region 9–12 acting as a nucleation site, and suggest that the kinetics of hybrid formation are largely dependent on the number of possible base pairs that could form between the oligonucleotide and the nucleation site. The results further suggest that nucleation initiating with the 3' terminus of the oligonucleotide is preferred over an internal oligonucleotide site (compare 91B and 92A). Similar results supporting this interpretation have also been obtained in SCAN reactions using other RNA-targets including the HIV TAR RNA.

Knowledge of the rate-limiting factors in SCAN reactions is important in guiding the design of oligonucleotides. The results described above suggest that a major rate-limiting factor is the initial interaction of the oligonucleotides with nucleation sites on the target RNA, including those within hairpin loops, bulges, internal loops and other regions. This property of the SCAN assay can be used to advantage, since loops and bulges are the preferred recognition sites of most RNA-binding proteins and may also be involved in tertiary RNA-RNA interactions such as pseudoknots. Such RNA-protein and RNA-RNA interactions are critical for the regulatory function of most RNA structures. Therefore, by careful choice of oligonucleotides, the SCAN assay can be made highly sensitive to ligands that interact with these regions. Furthermore, in larger multi-domain RNA structures, different oligonucleotides can be used to target different sub-domains of the RNA.

EXAMPLE 6

IDENTIFICATION OF SPECIFIC RNA-BINDING LIGANDS

SCAN reactions containing 100 nM radiolabeled AB-RNA and 250 nM biotinylated oligonucleotide 67B were incubated with increasing amounts of ATP or UTP as test ligands.

Figure 15:
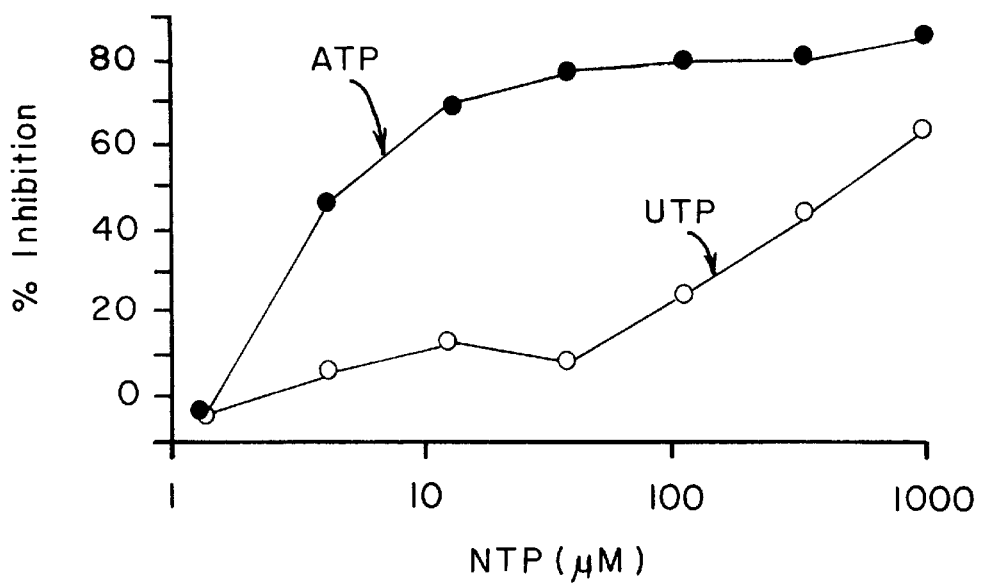
FIG. 15 is a graphic illustration of the effect of increasing concentrations of ATP or UTP on the formation of hybrids between radiolabelled AB RNA and biotinylated complementary 67B oligonucleotide. The data are shown as the percentage of inhibition of hybrid formation when compared to reactions in the absence of ligand.

In the absence of test ligand, 70% of AB-RNA was retained on NC-filters. Inhibition of RNA retention on NC-filters (% inhibition) was obtained as $(1-(R/R_0)X100)$, where $R_0$ is retention without test ligand and R is retention with test ligand. While 5 mM ATP inhibited retention by 50%, 500 mM UTP was needed to achieve the same effect showing a 100-fold specificity factor (FIG. 15).

Figure 16:
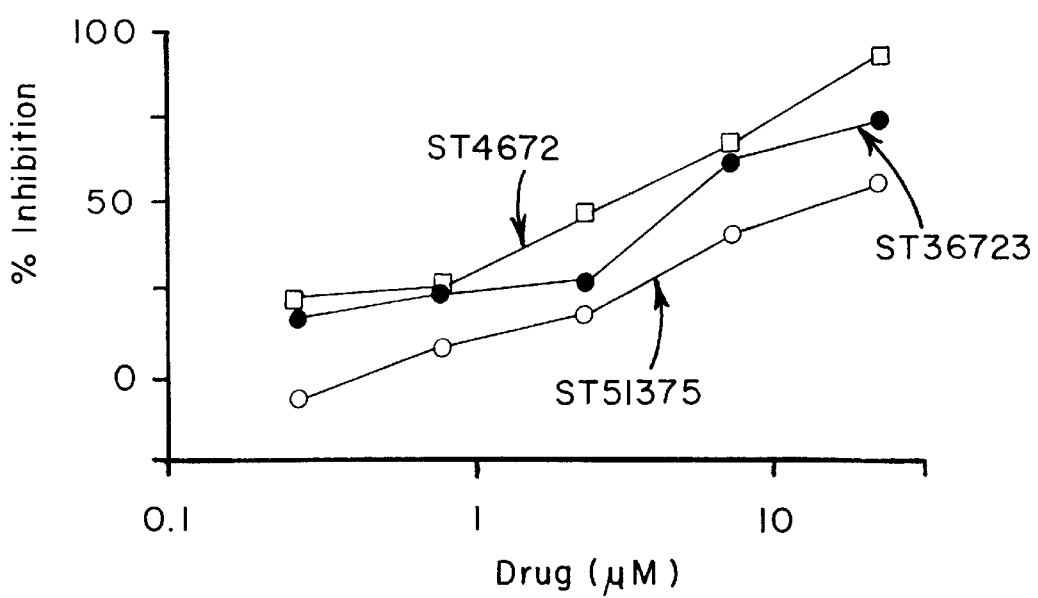
FIG. 16 is a graphic illustration of the effect of increasing concentrations of the indicated diphenylfuran derivatives on the formation of hybrids between RRE, RNA and a biotinylated complementary oligonucleotide. The data are shown as in FIG. 15.

Similarly, addition of RRE ligands ST36723, ST46172, and ST51378 inhibited RRE retention on NC-filters by 50% at 2.5–15 $\mu$M (FIG. 16). These ligands have been shown in separate experiments to interact specifically with RRE and to inhibit the Rev-RRE interaction at low micromolar concentrations.

Figure 17:
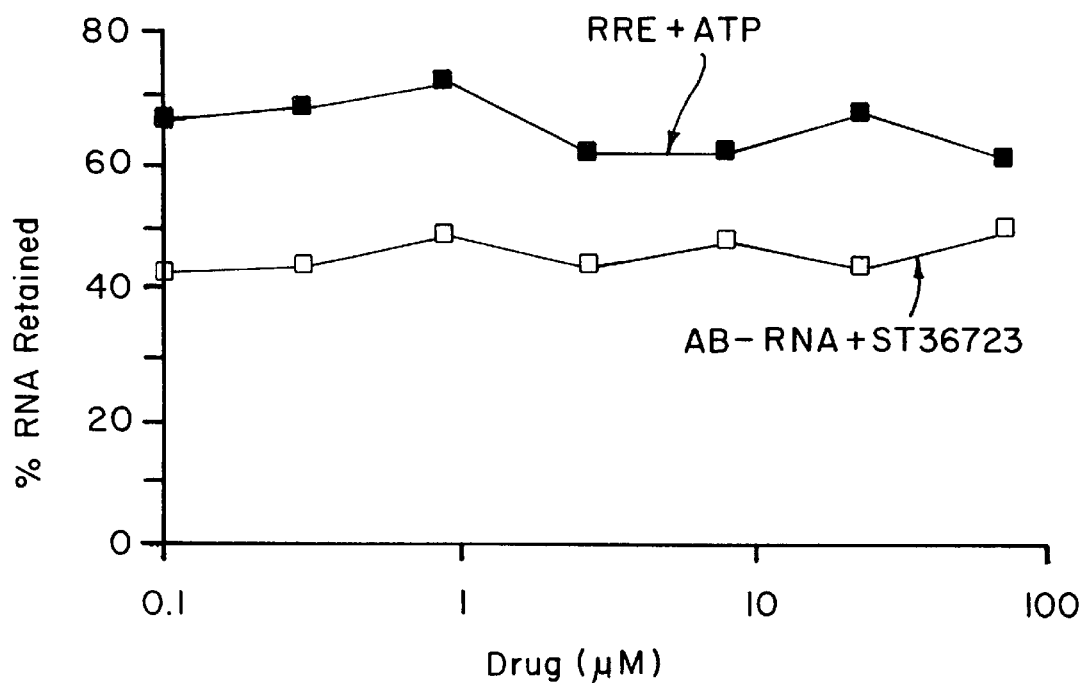
FIG. 17 is a graphic illustration of the effect of increasing concentrations of ATP on the formation of hybrids between RRE RNA and a biotinylated complementary oligonucleotide (closed squares); and the effect of increasing concentrations of the diphenylfuran derivative ST36723 on the formation of hybrids between radiolabelled AB RNA and biotinylated complementary 67B oligonucleotide (open squares).

The differential response of the AB RNA-containing SCAN assay to ATP and other NTPs reflects the specificity of the assay. In order to confirm this selectivity, known RNA ligands were tested in SCAN reactions using heterologous RNA targets. As shown in FIG. 17, ATP had no effect on RRE based SCAN reactions (closed squares). Conversely, the RRE ligand ST36723 did not affect the AB-RNA SCAN system (open squares).

EXAMPLE 7

OPTIMIZATION OF HIGH-THROUHGPUT SCREENING METHOD

The effect of different solvents and reagents on the high throughput screening reactions described above was tested.

DMSO is typically used as a solvent for distribution of compounds into assay plates. In practicing the present invention, DMSO is typically present at a concentration of 5% (v/v). Methanol and ethanol are also used as solvents for some compound collections including natural products. Dithiothreitol may be added to provide a reducing environment to prevent unwanted reactivity of some compounds.

Figure 18A:
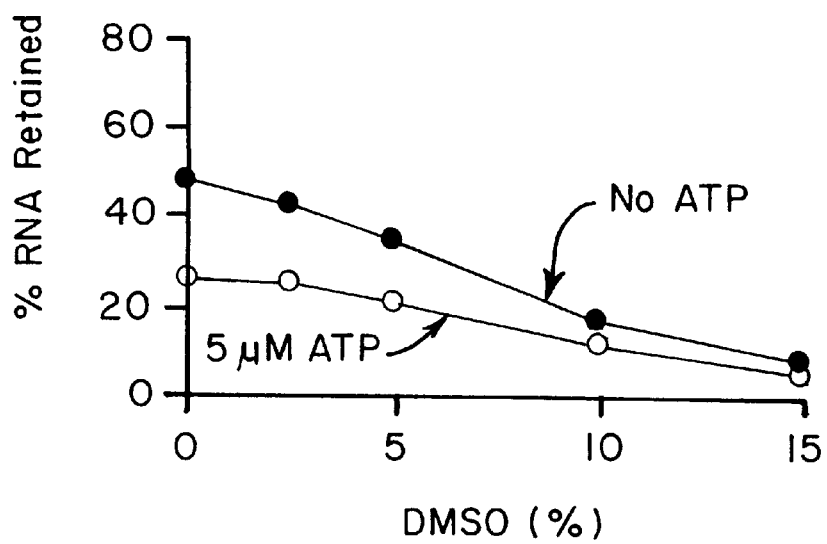
FIG. 18A is a graphic illustration of the effect of increasing concentrations of DMSO on the formation of hybrids between radiolabelled AB RNA and biotinylated complementary 67B oligonucleotide.
Figure 18B:
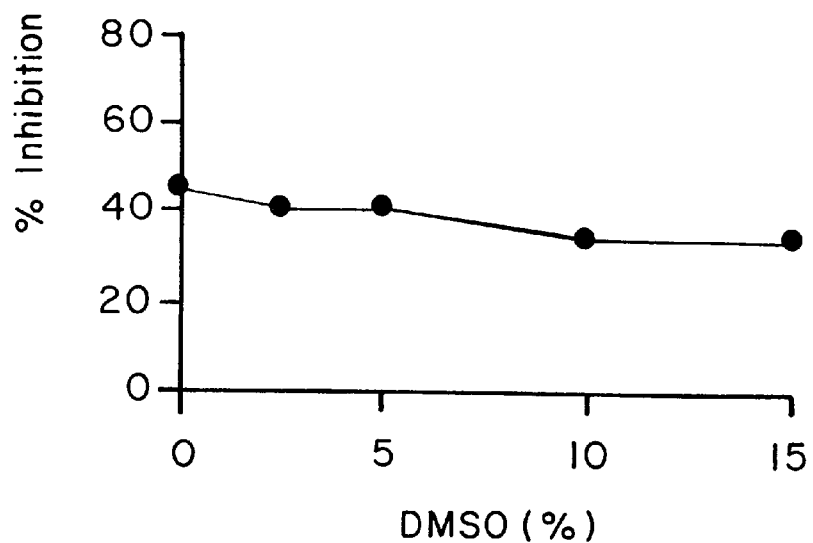
FIG. 18B is a graphic illustration of the effect of increasing concentrations of DMSO on the extent of inhibition by 5mM ATP on the formation of hybrids between radiolabelled AB RNA and biotinylated complementary 67B oligonucleotide.

Reactions containing 50 mM Tris pH 7.5, 200 mM NaCl, 10 mM $MgCl_2$, 100 nM AB-RNA, 1 µM yeast tRNA and 250 nM oligonucleotide 67B were performed in the presence of varying amounts of the reagents. Addition of increasing amounts of DMSO to the reactions resulted in a reduction in hybrid formation (FIG. 18A, closed circles), however the reaction remained sensitive to the addition of a specific ligand (FIG. 18A, open circles). Furthermore, the extent of inhibition obtained at various DMSO concentrations with 5 µM ATP as shown in FIG. 18A was not significantly affected by DMSO (FIG. 18B).

Figure 18C:
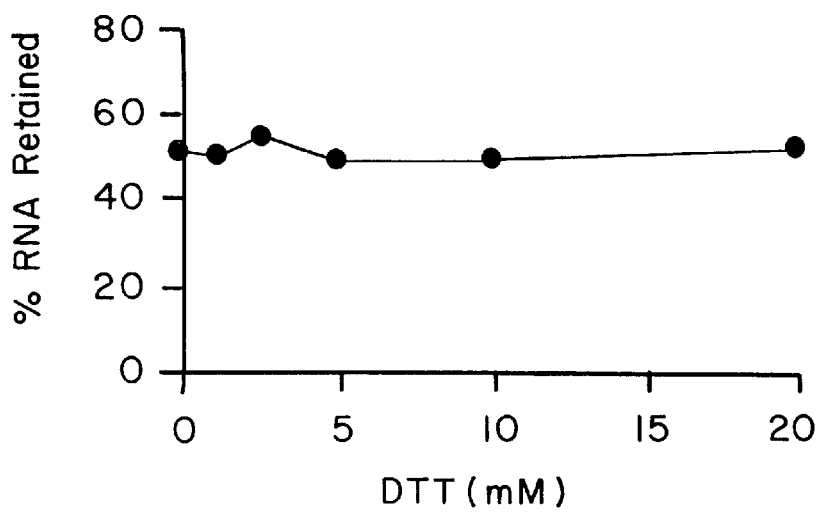
FIG. 18C is a graphic illustration of the effect of increasing concentrations of dithiothreitol on the formation of hybrids between radiolabelled AB RNA and biotinylated complementary 67B oligonucleotide.
Figure 18D:
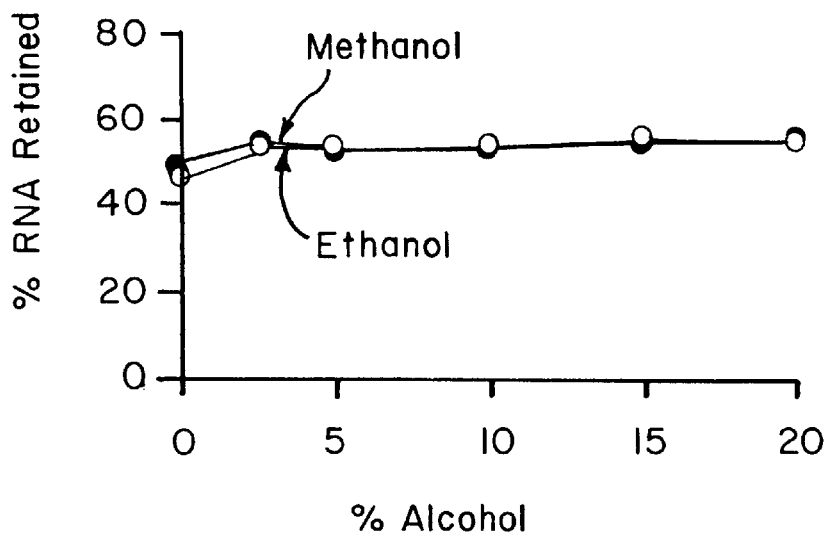
FIG. 18D is a graphic illustration of the effect of increasing concentrations of ethanol and methanol or the formation of hybrids between radiolabelled AB RNA and biotinylated complementary 67B oligonucleotide.

FIGS. 18C and 18D show that the SCAN reactions are not affected by various concentrations of DTT, methanol, or ethanol. Similar results were obtained using RRE as the RNA target.

These results show that the SCAN reactions have a good tolerance to solvents and reagents usually used in high throughput screening procedures.

The SCAN assay is fully compatible with a high throughput format involving automatic equipment and room temperature conditions. Delivery of reagents and filtration is performed with 96-well format automatic pipettors (Quadra-96 from Wallac Oy, Turku, Finland) equipped with a multiscreen vacuum manifold (Millipore, Bedford, Mass.), and scintillation counting is performed directly on the 96-well nitrocellulose filter plates (Millipore, Bedford, Mass.) in a 96-well format Micro-beta scintillation counter (Wallac Oy, Turku, Finland). Reaction conditions and other parameters have been optimized in order to keep reaction times within 0.5 and 2 hours. This procedure design allows a single scientist to screen up to 8,000 compounds per week.

Figure 19:
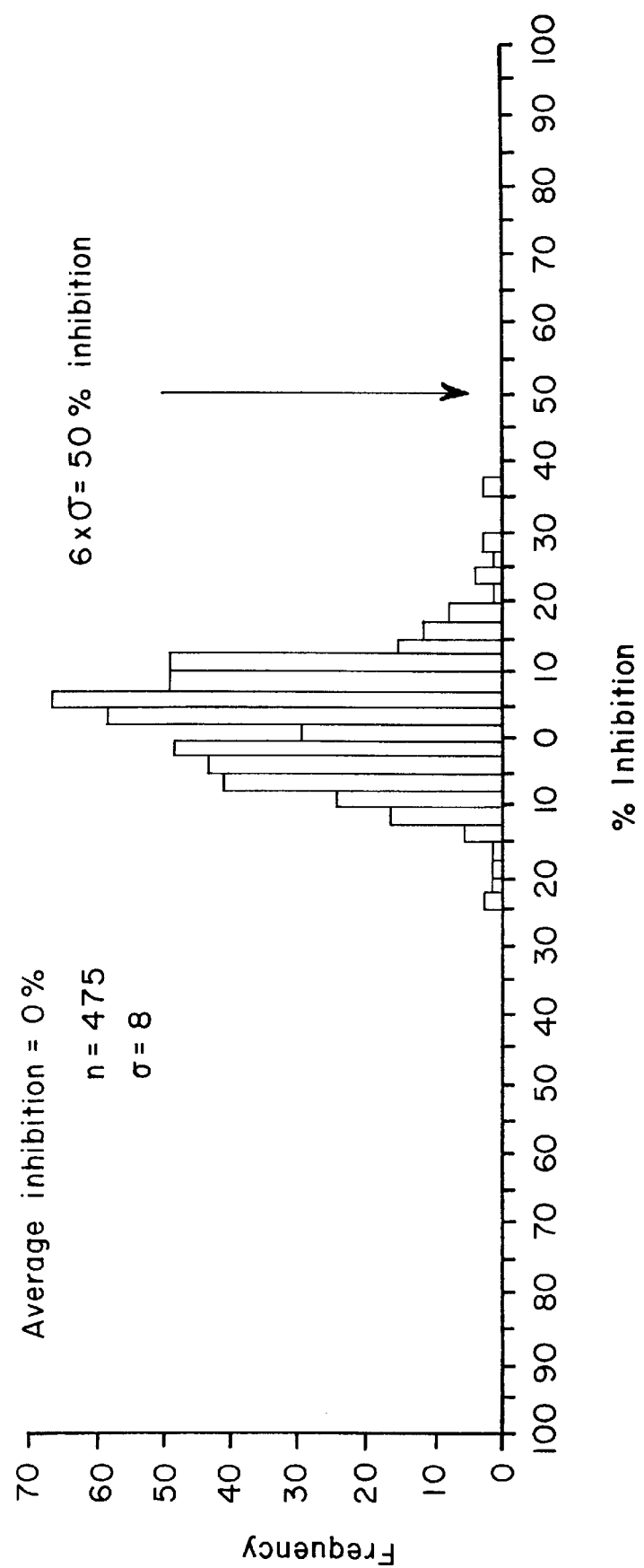
FIG. 19 is a graphic illustration of the reproducibility of the SCAN assay performed as in FIG. 18 above (5% DMSO).

FIG. 19 shows sample data obtained from 475 RRE SCAN reactions containing 5% DMSO in the absence of ligand. The assay is highly reproducible, with an average inhibition between of 0+/−8% in the absence of ligands. With a standard screening compound concentration of 20 µM, a "hit" is expected to inhibit hybrid formation by 50% and will be clearly distinguishable above the background "noise" level.

EXAMPLE 8

SCAN ASSAY UNDER EQUILIBRIUM CONDITIONS

The following experiment was performed to demonstrate a screening assay in which the oligonucleotide and ligand reach an equilibrium with the target RNA, i.e., the population of RNA:ligand and RNA:oligonucleotide complexes depends upon their relative dissociation constants. A screening assay having this configuration has the advantage of removing time constraints for various steps in the assay. In addition, thermodynamic parameters associated with ligand binding can be more easily derived from the results of the assay.

Figure 20:
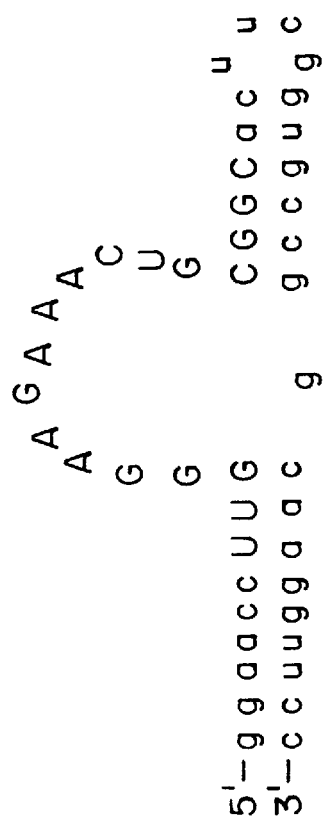
FIG. 20 (top panel) is an illustration an ATP-binding target RNA showing in bold-face uppercase the sequences complementary to the biotinylated oligonucleotide used. The bottom panel is a graphic illustration of the time course of hybrid formation (A) and dissociation (D) under equilibrium conditions.
Figure 20:
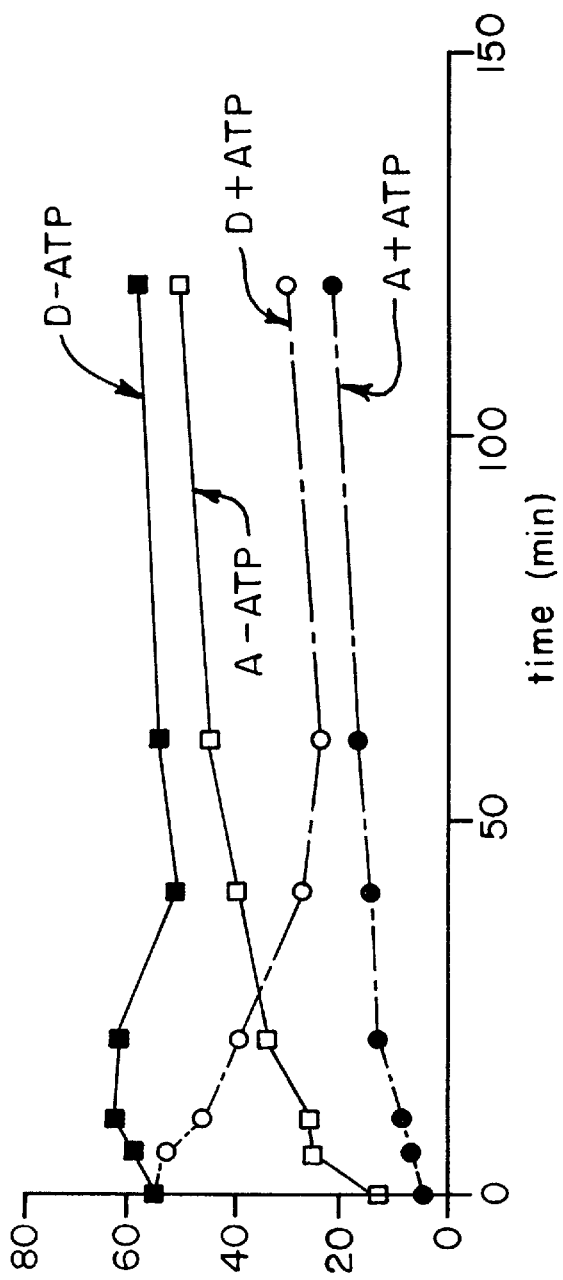

Using a series of oligonucleotides of various length and target sites comprising AB RNA, a group of oligonucleotides has been identified that fully equilibrated with ATP (an example is shown in FIG. 20, top panel). The oligonucleotide used is complementary to the sequence shown in bold-faced letters (FIG. 20, top panel).

Target RNA:oligonucleotide complexes were pre-formed by incubated a solution containing 100 nM AB RNA and 500 nM oligonucleotide for 2 h at 25° C. Dissociation was initiated by diluting the reaction 5-fold in the presence or absence of 100 µM ATP (resulting in final concentrations of AB RNA, 20 nM; oligonucleotide, 100 nM; ATP, 100 µM). Binding of hybrids to nitrocellulose filters was performed as described above.

The results (presented as % oligo:RNA complex) indicate that approximately 60% inhibition by ATP is observed, comparable to what is found using a kinetic assay (i.e., under non-equilibrium conditions).

EXAMPLE 9

LIGAND BINDING INDUCES CONFORMATIONAL CHANGES IN RNA

The experiment described below was performed to monitor the stabilization of an RNA structure upon ligand binding. In this experiment, absorbance at 260 nM was monitored as the temperature of the sample was increased. The increase in temperature causes the RNA to unfold, thereby allowing individual bases to absorb more ultraviolet light.

Figure 21:
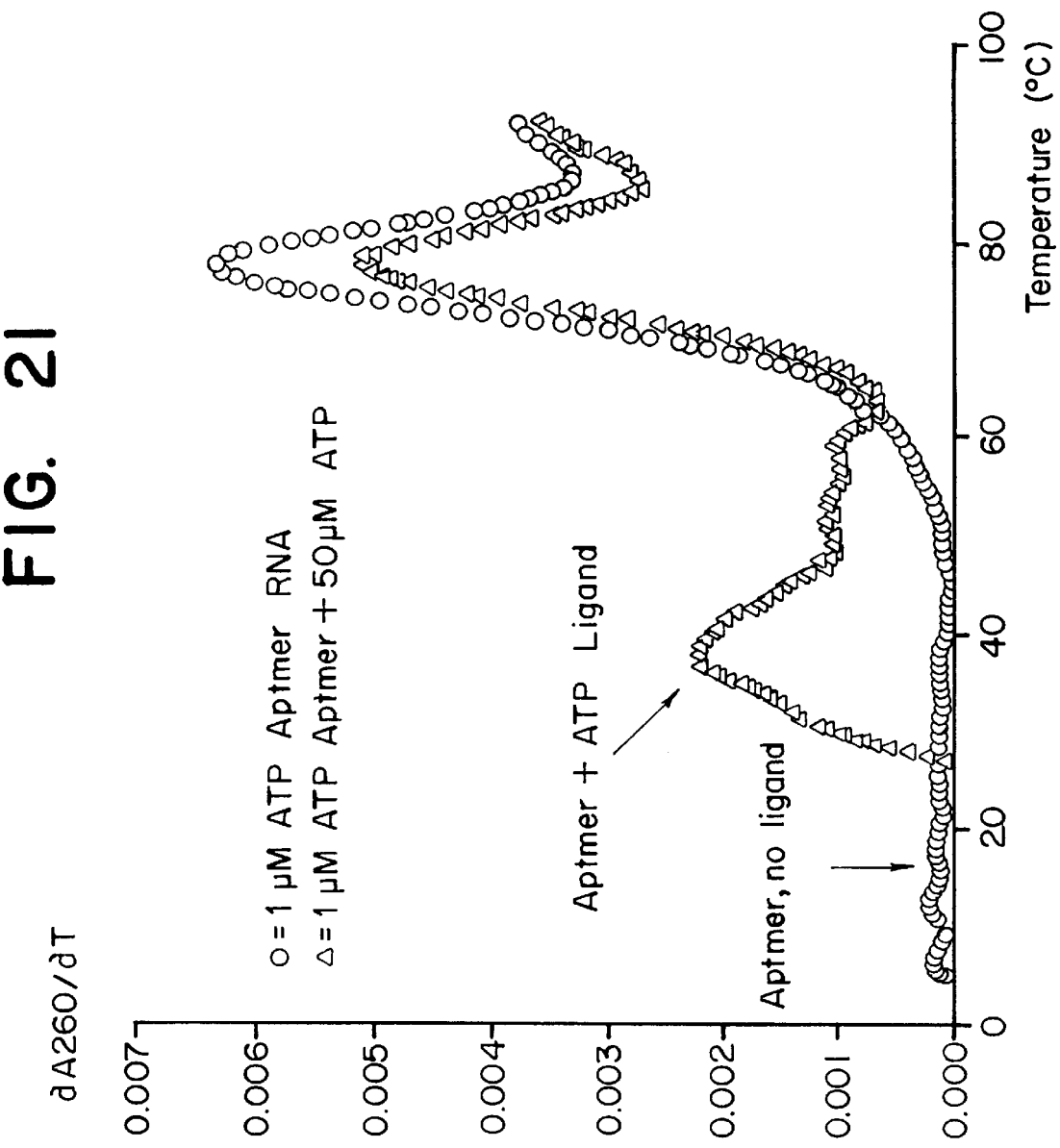
FIG. 21 is a graphic illustration of the effect of temperature on the absorbance of AB RNA in the absence and presence of ATP.

The results are graphically illustrated as the first derivative of the absorbance with respect to change in temperature (FIG. 21). The data indicate a new and obvious transition centered at 40° C. which occurs only in the presence of ATP. These results indicate that the ATP ligand stabilizes the RNA structure.

EXAMPLE 10

HIGH-THROUGHPUT DETECTION OF RNA LIGANDS USING FLUORESCENCE ENERGY TRANSFER

Fluorescence energy transfer (FET) is based on the existence of pairs of fluorescence donor and acceptor molecules in which fluorescence emission by the donor probe is transferred directly to an acceptor probe in close proximity to the donor probe. Thus, upon excitation of the donor probe, a reduction in donor emission and increase in acceptor emission relative to the probes alone is observed if the probes are sufficiently close. The efficiency of energy transfer is inversely proportional to the sixth power of the distance between the donor and acceptor probes, thus the extent of these effects can be used to calculate the distance separating the probes. Intramolecular FET has been used to probe the structure of transfer RNA molecules (Beardsley et al., Proc. Natl. Acad. Sci. USA, 65:39, 1970). In the present invention, FET is used to monitor a change in target RNA conformation. The only requirement is that the distance between the donor and acceptor probes must differ significantly between the different conformations.

A. Several embodiments of the present invention in which FET is used are described below.

1) FIG. 22 shows a relatively simple ABC stem-loop RNA structure. A synthetic RNA target is prepared containing complementary sequences B'A' and C'B' (FIG. 23). This synthetic substrate is also double-labelled with Fluorescein (F) and Rhodamine (R) at the 5' and 3'-ends, respectively. This RNA may achieve two possible structures (FIG. 23, left and right). One of these structures positions the fluorescent dyes in close proximity favoring FET.

The RNA is designed so that the distance between F and R (FIG. 23, right) is minimal. This ensures maximum FET difference between the two structures and obviates the need for a complementary DNA oligonucleotide to maintain an appropriate F-R distance in the structure in FIG. 23, left.

2) FIG. 24 shows a similar ABC stem-loop structure in its folded (left) and unfolded (right) configurations. The lack of an alternative structure requires that the stem-and-loop structure must be intrinsically unstable, so that a difference in FET can be detected when the stem-loop is stabilized by a binding of a ligand.

3) FIG. 25 shows a target RNA molecule containing multiple discrete target structures (X, Y and Z). In this case, the use of a relatively long DNA oligonucleotide will increase the FET difference between the folded RNA and the hybrid.

Figure 26:
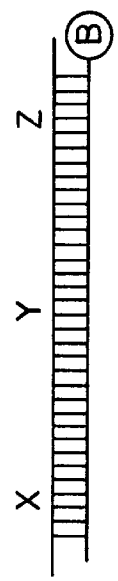
FIG. 26 is a graphic illustration of the hybridization reaction between a complex labelled RNA structure and a biotinylated oligonucleotide.
Figure 26:
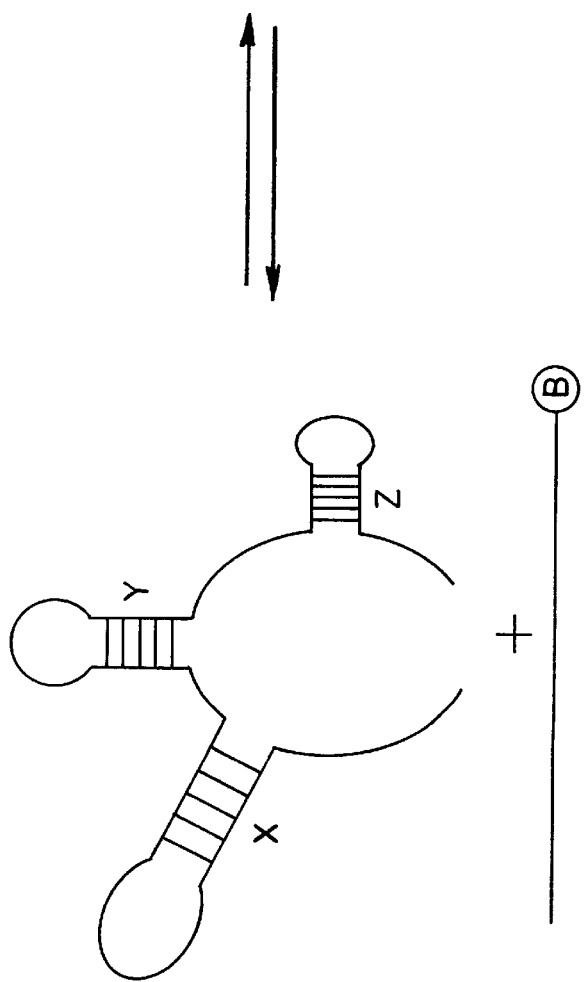

Alternatively, a "capture measure" method may be used, as illustrated in FIG. 26. In this embodiment, the target RNA is labelled with a radioisotope or a fluorofor, and the DNA oligonucleotide is biotinylated. The amount of hybrid is measured by capture with streptavidin-coated beads in conjunction with SPA, or any one of the SA-based methods described above.

Figure 27:
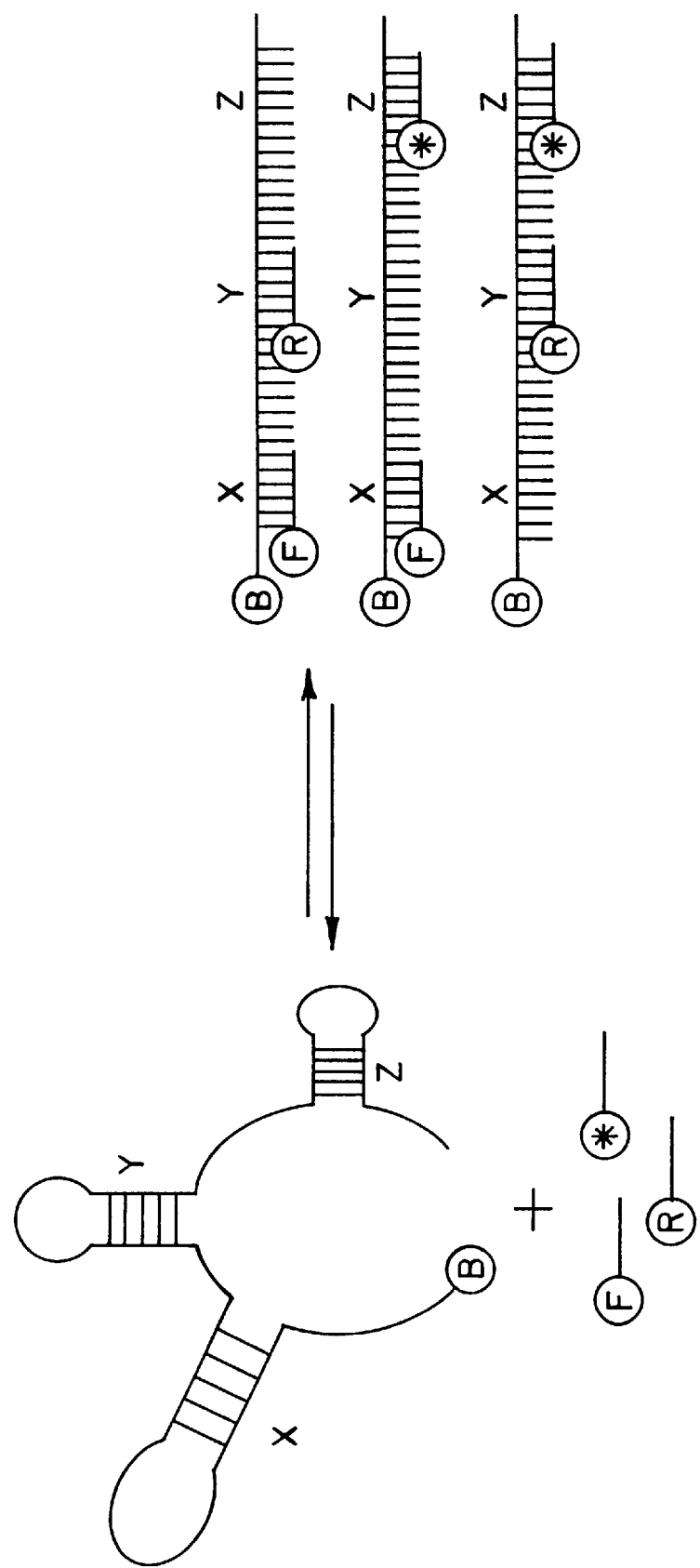
FIG. 27 is a graphic illustration of the hybridization reaction between a complex biotinylated RNA structure and individual oligonucleotides complementary to different regions of the RNA.

To avoid potential problems caused by the formation of partial hybrids, multiple discrete DNA strands directed to each of the target sites could be used. In this embodiment, the RNA carries the biotin tag, while each DNA strand is labeled with a different label such as Fluorescein (F), texas red (R) and $P^{32}$ (P) (FIG. 27). In this way, multiple targets within the same RNA molecule could be tested simultaneously by measuring each one with a different method.

Figure 28A:
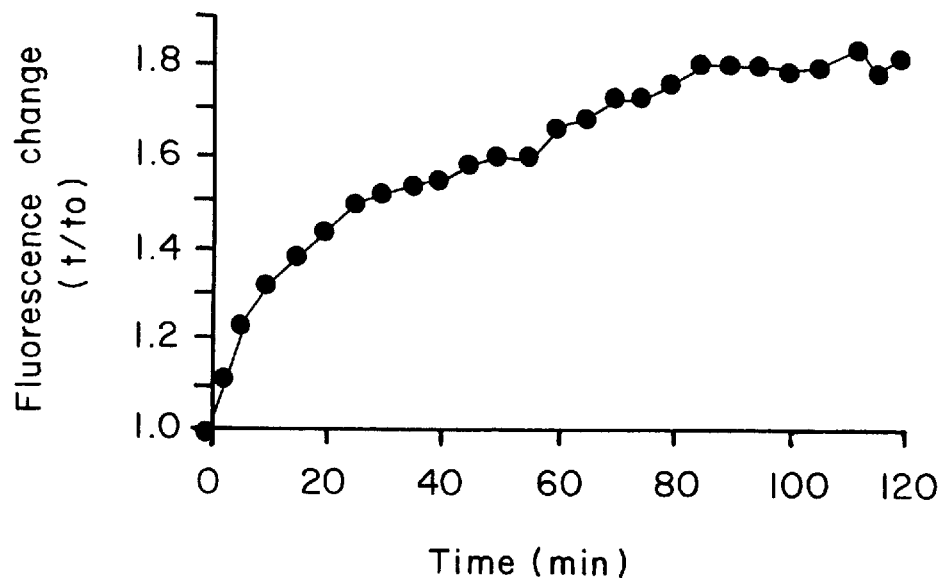
FIG. 28A is a graphic illustration of the time course of change in fluorescence of fluorescein-labelled AB RNA during incubation with an unlabelled complementary oligonucleotide (67B).

B. Experimental results: While developing a SCAN assay based on FET between 3'-fluorescein labeled AB-RNA (AB-RNA-F) and a 5'-rhodamine labeled oligonucleotide, it was unexpectedly observed in a control experiment that a substantial increase in fluorescein emission at 535 nm occurred upon addition of an oligonucleotide carrying no fluorescent labels (FIG. 28A). Reactions containing 50 mM Tris pH 7.5, 200 mM NaCl, 10 mM $MgCl_2$, and 60 nM AB-RNA-F were monitored at 535 nm emission (485 nm excitation) in a CytoFluor II fluorescence multi-well plate reader (PerSeptive Biosystems, Framingham, Mass.) for increasing times after the addition of oligonucleotide 67B.

The results suggested that the fluorescein emission was quenched as a result of the association of the fluorescein moiety with the structure of AB-RNA. In order to estimate the maximum achievable change in fluorescence emission at 535 nm resulting from the association of the fluorescein moiety and the RNA, the emission at 535 nm was measured during the course of RNAse A digestion of AB-RNA-F; it was found that it increased to a maximum of 2-fold over the initial value.

Figure 28B:
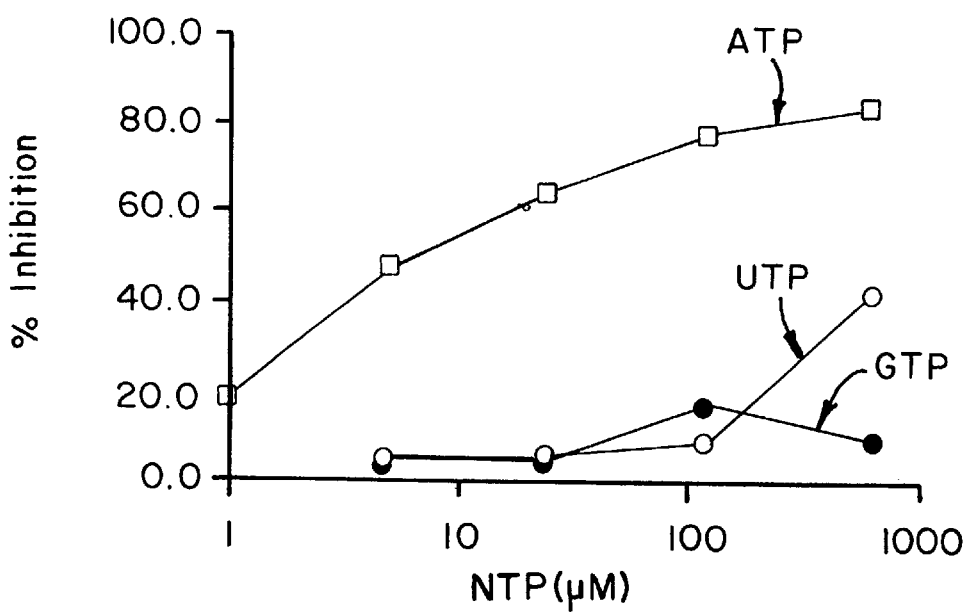
FIG. 28B is a graphic illustration of the effect of ATP, GTP, and UTP on the fluorescence increase shown in FIG. 28A.

Because of the high reproducibility and sensitivity of fluorescence spectrophotometers, a 2-fold increase in fluorescence represents more that sufficient change in signal to use it as a sensitive assay. Therefore, the effect of ATP, GTP and UTP was tested in SCAN reactions containing AB-RNA-F and the unlabeled oligonucleotide 67B (FIG. 28B).

The results indicate that the addition of ATP specifically inhibited the fluorescence increase observed in the absence of added ligand. The IC50 value (5 mM) for ATP in this assay was identical to the value obtained with the SAAP based SCAN assay. As expected, UTP had some effect at much higher concentrations while GTP had no effect at all. Accordingly, these data demonstrate the suitability of this approach for measuring hybrid formation in SCAN reactions.

What is claimed is:

1. A high-throughput method for identifying a ligand that binds a predetermined target RNA sequence, which comprises:
   (a) selecting as test ligands a plurality of compounds not known to bind to the target RNA sequence;
   (b) incubating the target RNA sequence in the presence of each of said test ligands to produce a test combination;
   (c) incubating the target RNA sequence in the absence of a test ligand to produce a control combination;
   (d) detecting the conformation of the target RNA sequence in each combination;
   (e) selecting as a ligand any test ligand that causes a measurable change in the target RNA conformation in the test combination relative to the target RNA conformation in the control combination; and
   (f) repeating steps (b)–(e) with a plurality of said test ligands to identify a ligand that binds to the target RNA sequence.

2. The method of claim 1, wherein the measurable change in the target RNA conformation comprises a change in the target RNA conformation from less folded to more folded, from more folded to less folded, or from a first folded conformation to a second, alternative, folded conformation.

3. The method of claim 1, further comprising prior to and/or during step (d), subjecting the test and control combinations to conditions that denature a detectable fraction of the target RNA sequence in the control combination.

4. The method of claim 3, wherein the subjecting comprises at least one of altering the temperature, altering the salt concentration, adding denaturing compounds, and combinations thereof.

5. The method of claim 1, wherein the target RNA is from about 5 to about 500 nucleotides in length.

6. The method of claim 1, wherein the target RNA comprises a label selected from the group consisting of a radionuclide, a fluorescent compound, an affinity label, and combinations thereof.

7. The method of claim 1, wherein the measuring step comprises the steps of:
   (i) contacting the test and control combinations with an oligonucleotide under conditions in which the oligonucleotide preferentially hybridizes to a predetermined conformation of the target RNA sequence; and
   (ii) measuring the fraction of the target RNA sequence present in hybrids with the oligonucleotide,
   wherein the fraction measured in (ii) indicates the fraction of the target RNA in said predetermined conformation.

8. The method of claim 7, wherein the oligonucleotide comprises a label selected from the group consisting of a radionuclide, a fluorescent compound, an affinity label, and combinations thereof.

9. The method of claim 1, wherein the target RNA sequence further comprises a first fluorescence moiety and a second fluorescence moiety, wherein (i) the fluorescence emission wavelength maximum of the first moiety overlaps the fluorescence absorption wavelength maximum of the second moiety, and (ii) the first moiety and the second moiety are positioned in the target RNA so that fluorescence energy transfer between the first and second moieties occurs only when the target RNA is in a predetermined conformation.

10. A method for identifying ligands that bind a predetermined target RNA sequence, which comprises:

(a) identifying a library comprising test ligands not known to bind to a predetermined target RNA sequence;

(b) selecting a subset of test ligands in the library;

(c) incubating the target RNA in the presence of at least one selected test ligand to produce at least one test combination;

(d) incubating the target RNA in the absence of each selected test ligand to produce corresponding control combinations;

(e) detecting the conformation of the target RNA in each pair of corresponding test and control combinations under the same assay conditions;

(f) identifying as a ligand any test ligand from any test combination wherein the target RNA exhibits a different conformation than the target RNA in the corresponding control combination; and (g) repeating steps (b)–(e) in a high throughput screen.

11. The method of claim 10, wherein the measurable change in the target RNA conformation comprises a change in the target RNA conformation from less folded to more folded, from more folded to less folded, or from a first folded conformation to a second, alternative, folded conformation.

12. The method of claim 10, wherein the assay conditions comprise subjecting the test and control combinations to conditions that denature a detectable fraction of the target RNA sequence in the control combination.

13. The method of claim 10, wherein the assay conditions comprise at least one of altering the temperature, altering the salt concentration, adding denaturing compounds, and combinations thereof.

14. The method of claim 10, wherein the target RNA is from about 5 to about 500 nucleotides in length.

15. The method of claim 10, wherein the target RNA comprises a label selected from the group consisting of a radionuclide, a fluorescent compound, an affinity label, and combinations thereof.

16. The method of claim 10, wherein the detecting step comprises the steps of:

(i) contacting the test and control combinations with an oligonucleotide under conditions in which the oligonucleotide preferentially hybridizes to a predetermined conformation of the target RNA; and (ii) measuring the fraction of the target RNA sequence present in hybrids with the oligonucleotide, wherein the fraction measured in (ii) indicates the fraction of the target RNA in said predetermined conformation.

17. The method of claim 16, wherein the oligonucleotide comprises a label selected from the group consisting of a radionuclide, a fluorescent compound, an affinity label, and combinations thereof.

18. The method of claim 10, wherein the target RNA sequence further comprises a first fluorescence moiety and a second fluorescence moiety, wherein (i) the fluorescence emission wavelength maximum of the first moiety overlaps the fluorescence absorption wavelength maximum of the second moiety, and (ii) the first moiety and the second moiety are positioned in the target RNA so that fluorescence energy transfer between the first and second moieties occurs only when the target RNA is in a predetermined conformation.

19. A method according to claim 1 wherein at least 0.1 to 1 percent of the test ligands are identified as ligands.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 64 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

GGAACCTTAG CCGGCACCGA AGTGCCGCAG TTTCTTCCCA AGGTTCCTAT AGTGAGTCGT      60

ATTA      64

(2) INFORMATION FOR SEQ ID NO:2:

```
    (i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

GAAUACUAUG GGCGCAGCGU CAAUGACGCU GACGGUACAG GCCAGACAAU UAUUGUCUGG          60

UAUAGU                                                                    66

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

CGTCATTGAC GCTGCGCCC ATAGTG                                               25
```